US006333155B1

(12) United States Patent
Lockhart et al.

(10) Patent No.: US 6,333,155 B1
(45) Date of Patent: Dec. 25, 2001

(54) EXPLOITING GENOMICS IN THE SEARCH FOR NEW DRUGS

(75) Inventors: David J. Lockhart, Del Mar; Lisa Wodicka, San Diego; Ming Hsiu Ho, San Jose, all of CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 09/215,207

(22) Filed: Dec. 18, 1998

Related U.S. Application Data

(60) Provisional application No. 60/068,289, filed on Dec. 19, 1997.

(51) Int. Cl.[7] .............................. C12Q 1/68; C12P 19/34; C07H 21/02; C07H 21/04
(52) U.S. Cl. ........................ 435/6; 435/91.2; 536/23.1; 536/24.3; 536/24.31; 536/24.33; 935/6; 935/18
(58) Field of Search ...................... 435/6, 91.2; 536/23.1

(56) References Cited

U.S. PATENT DOCUMENTS 5,700,637 A 12/1997 Southern ........................... 435/6

FOREIGN PATENT DOCUMENTS

| WO | 89/10977 | 11/1989 |
| WO | 97/10365 | 3/1997 |
| WO | 97/27317 | 7/1997 |
| WO | 97/29091 | 8/1997 |
| WO | 98/05335 | 2/1998 |

OTHER PUBLICATIONS

Ecker et al., "Estimation of the chemosensitizing activity of modulators of multi–drug resistance via combined simultaneous analysis of sigmoidal–dose response curves", *J. Pharmacy and Pharmacology*, vol. 49, pp. 305–309, Jan. 1997.*

Stephen Fodor "Massively parallel genomics" Science vol. 277, Jul. 18, 1997 pp. 393–394.

Sedlak et al. "Gene Chip Technology Ready to Impact Diagnostic Markets" Genetic Engineering News, Dec. 1997, p. 1.

Lockhart et al. "Expression monitoring by hybridization to high–density oligonucleotide arrays" Nature Biotechnology, vol. 14, Dec. 1996, pp. 1674–1680.

Schow et al. "Synthesis and Activity of 2,6,9–Trisubstituted Purines" Bioorganic & Medicinal Chemistry Letters, vol. 7, No. 21, pp. 2697–2702 1997.

Konig et al. "The novel cyclin–dependent kinase inhibitor flavopiridol downregulates Bcl–2 and induces growth arrest and apoptosis in chronic B–cell leukemia lines" Blood vol. 90, No. 11, 1997 pp. 4307–4312.

De Azevedo et al. "Inhibition of cyclin–dependnet kinase by purine analogues Crystal Structure of human cdk2 complexed with roscovitine" European Journal of biochemistry, vol. 243, No. 1/02, 1997 pp. 518–526.

Norman et al. "A structure–based library approach to kinase inhibitors" The Journal of the American Chemical Society, vol. 118, 1996 pp. 7430–7431.

Brooks et al. "CVT–313, a specific and potent inhibitor of CDK2 that prevents neointimal proliferation" Journal of Biological Chemistry, vol. 272, No. 46, Nov. 14, 1997 pp. 29207–29211.

Gray "Exploiting chemical libraries, structure, and genomics in the search for kinase inhibitors" Science, vol. 281, 1998 pp. 533–538.

\* cited by examiner

*Primary Examiner*—Jeffrey Fredman
*Assistant Examiner*—Arun Kr. Chakrabarti
(74) *Attorney, Agent, or Firm*—Banner & Witcoff

(57) ABSTRACT

The cellular effects of potentially therapeutic compounds are characterized in mammalian cells and yeast. In the latter case the effects can be characterized on a genome-wide scale by monitoring changes in messenger RNA levels in treated cells with high-density oligonucleotide probe arrays.

14 Claims, 6 Drawing Sheets

(3 of 6 Drawing Sheet(s) Filed in Color)

1. Amination at C-6 ($^1RNH_2$) and/or
   Alkylation at N-9 ($^2ROH$) and/or
   Amination at C-2 ($^3RNH_2$)
2. Acidic cleavage Flavopiridol Olomoucine ($^1R = H$, $^2R = CH_3$)
Roscovitine ($^1R = CH_2CH_3$, $^2R = CH(CH_3)_2$)

Purvalanol A (R = H)
Purvalanol B (R = $CO_2H$)

Compound 40

Compound 100 (R = $CH_3$)
101 (R = H)

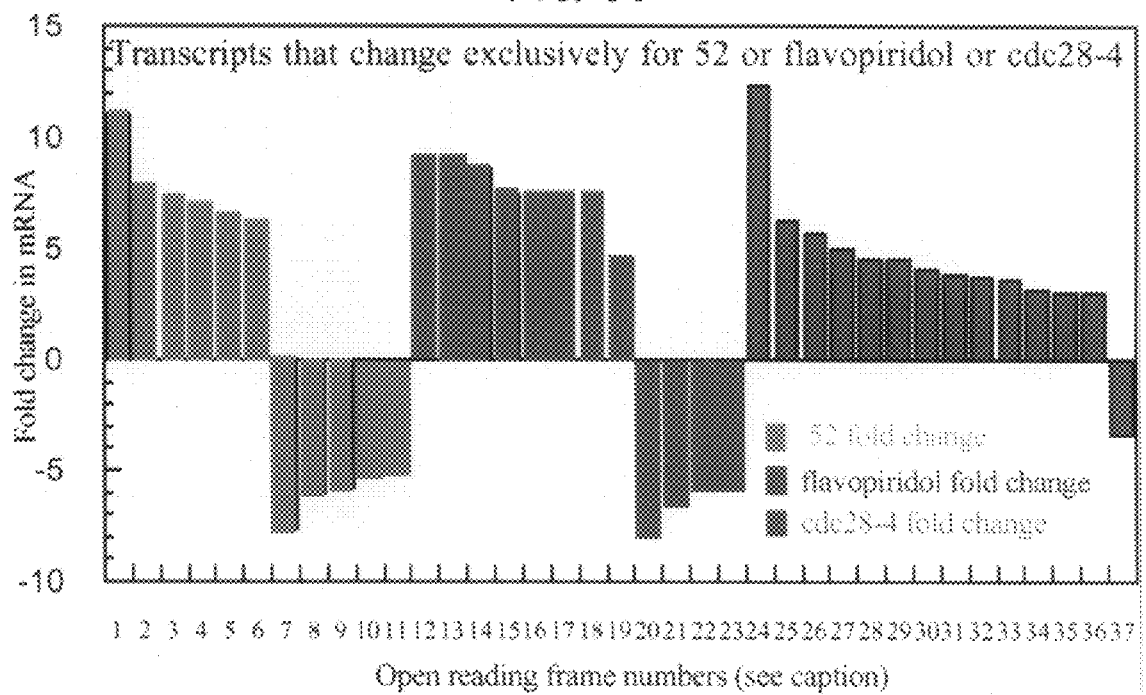

EXPLOITING GENOMICS IN THE SEARCH FOR NEW DRUGS

This Application benefit of provisional No. 60/068,289 filed Dec. 19, 1997.

BACKGROUND OF THE INVENTION

Many biological functions are accomplished by altering the expression of various genes through transcriptional (e.g. through control of initiation, provision of RNA precursors, RNA processing, etc.) and/or translational control. For example, fundamental biological processes such as cell cycle, cell differentiation and cell death, are often characterized by the variations in the expression levels of groups of genes.

Changes in gene expression also are associated with pathogenesis. For example, the lack of sufficient expression of functional tumor suppressor genes and/or the over expression of oncogene/protoncogenes could lead to tumorgenesis (Marshall, Cell, 64: 313–326 (1991); Weinberg, Science, 254: 1138–1146 (1991), incorporated herein by reference for all purposes). Thus, changes in the expression levels of particular genes (e.g. oncogenes or tumor suppressors) serve as signposts for the presence and progression of various diseases.

Often drugs are screened and prescreened for the ability to interact with a major target without regard to other effects the drugs have on cells. Often such other effects cause toxicity in the whole animal, which prevent the development and use of the potential drug. Therefore, there is a need in the art to develop a systematic approach to test and develop new drugs for their effects on cellular metabolism without relying on gross morphologic and phenotypic effects.

SUMMARY OF THE INVENTION

This invention provides methods and compositions for studying the complex relationships among drugs and genes. In some of its specific applications, this invention provides methods and compositions for detecting alternate targets for drug screening and development by monitoring the expression of genes affected by a drug or mutation.

BRIEF DESCRIPTION OF THE DRAWINGS

The file of this patent contains at least one drawing executed in color. Copies of this patent with color drawings are provided to the Patent and Trademark Office with payment of the necessary fee.

FIG. 2.

FIG. 3. Representative transcripts observed to change more than twofold for triplicate hybridizations for each of two independent experiments (except for cdc28-4, which represents triplicate hybridizations of RNA from a single experiment). (FIG. 3C) Transcripts that change for cdc28-4, cdc28-4 and 52, cdc28-4 and flavopiridol, and 52: YBR147W (unknown, has 7 potential transmembrane domains); YOL155C (unknown, similar to glucan 1,4-glucosidase); YJR127C (ZMS1, similar to Arp1p, an N-acetyltransferase); YKL109W (HAP4, transcriptional activator protein involved in activation of CCAAT box-containing genes); YBL015w (ACH1, acetyl-coenyme A hydrolase); YPR160W (GPH1, glycogen phosphorylase); YAL039C (CYC3, cytochrome c heme lyase); YML116W (ATR1, member of major facilitator superfamily); YCL009C (ILV6, acetolactate synthase regulatory subunit); YDR281C (unknown); YGL121C (unknown); YKL071w (unknown, similar to bacterial protein csgA); YLR311C (unknown); YER037w (unknown); YOR248W (unknown). *Names marked by an asterisk indicate open reading frames for which at least one hybridization of the set indicated a slightly less than twofold change in abundance.

DETAILED DESCRIPTION OF THE INVENTION

In addition to measuring the inhibitory effects of purine derivatives in kinase assays and assays of cell growth, their effects on the mRNA levels of nearly all yeast genes were determined with high-density oligonucleotide expression arrays (17, 18). These arrays (19, 20) make it possible to measure quantitatively and in parallel mRNA levels for a very large number of genes after any chemical, environmental, or genetic perturbation. Because purvalanol analogs inhibit both human and S. cerevisiae CDKs, transcript profiles were obtained in yeast, where they can be measured on a genome-wide scale.

Compounds 52 and flavopiridol were profiled to examine the effects of two structurally different Cdc28p active site inhibitors on gene expression. Compound 52Me was profiled as a control to determine which transcriptional changes result from treatment with a structurally similar compound with greatly diminished CDK activity. Yeast cultures were grown to late logarithmic phase (15), treated with 25 $\mu$M concentrations of the inhibitors for 2 hours, after which cellular polyadenylated mRNA was isolated and converted to biotin-labeled complementary RNA (cRNA) (17, 18). The labeled cRNA was then hybridized to a set of four arrays containing more than 260,000 25-nucleotide oligomers (20).

Figure 3A:
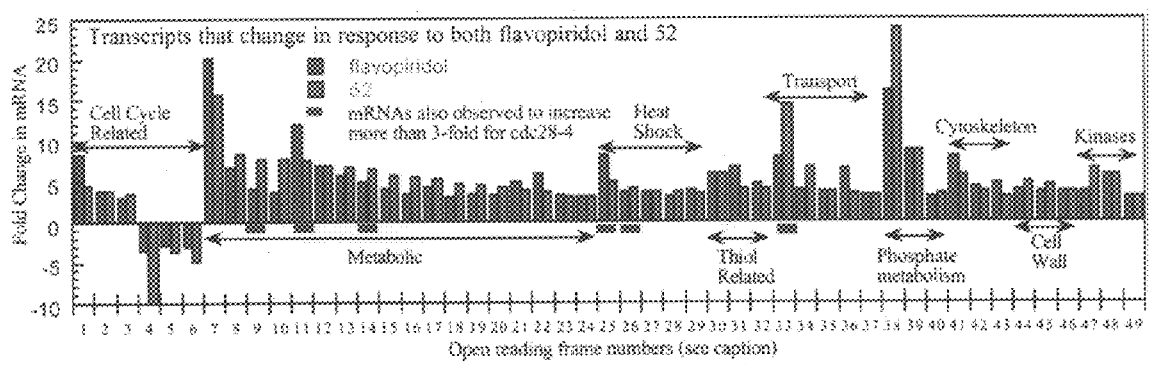
(FIG. 3A) Names of the genes whose mRNA levels change in common to 52 and flavopiridol (none of these transcripts changed significantly in the 52Me profile): YBR214w (similar to Schizosaccharomyces pombe protein moc1 involved in meiosis and mitosis); YGR108W (CLB1, $G_2$-M phase cyclin); YBL003c (HTA2, histone); YBL002w (HTB2, histone); YNL327W(EGT2, involved in timing of cell separation); YLR286C* (CTS1, endochitinase); YJL157C* (FAR1, inhibitor of Cdc28p/Cln1,2p complexes); YPR119W* (CLB2, $G_2$-M phase cyclin); YHR096C (HXT5, homologous to hexose transporters); YAL061W (unknown, similar to alcohol or sorbitol dehydrogenase); YKR097W (PCK1, phosphoenol pyruvate carboxykinase); YGR043C (similar to Tal1p, a transaldolase); YMR105C (PGM2, phosphoglucomutase); YBR169c (SSE2, heat shock protein of HSP70 family); YBR072W (HSP26, heat shock protein induced by osmostress); YLL026W (HSP104); YCR021c (HSP30); YPL240C (HSP82, chaperonin homologous to Escherichia coli HtpG); YDR171W (HSP42, involved in restoration of cytoskeleton during mild stress); YOR328W (PDR10, member of the ATP binding cassette superfamily); YDR406w (PDR15); YDL223c (unknown); YER 150w (similar to SedIp an abundant cell surface glycoprotein); YGR032W (GSC2, component of -1,3-glucan synthase); YGL179C* (serine-threonine kinase similar to Elm1p and Kin82p); YLR178C (TFS1, Cdc25-dependent nutrient and ammonia response cell cycle regulator); YNR009W (unknown); YFL031W (HAC1, basic leucine zipper protein, activates unfolded-protein response pathway); and YHR143W (unknown).

Out of more than 6200 genes monitored, 194 (3% of transcripts), 2 (0.03% of transcripts), and 132 (2% of transcripts) showed a greater than twofold change in transcript level when treated with 52, 52Me, or flavopiridol, respectively (21). Consistent with the diminished activity of 52Me both in vivo and in vitro, far fewer transcripts were affected by compound 52Me than by the CDK inhibitors. Of the 63 transcripts that changed in response to both CDK inhibitors 52 and flavopiridol, only nine were down-regulated, five of which (CLB1, CLB2, HTA2, HTB2, EGT2) were associated with cell cycle progression (FIG. 3A). The transcript encoded by CLB1 (G2 cyclin, implicated in the transition into mitosis) showed a significant decrease, consistent with inhibition of the Cdc28p-Clb1/2p kinase, which is involved in a positive feedback loop driving CLB1/2 transcription (22). Similarly, CDK activity has been implicated in transcriptional regulation of histone genes including HTA2 and HTB2 (23), and EGT2, a gene involved in the timing of cell separation after cytokinesis.

Figure 3B:
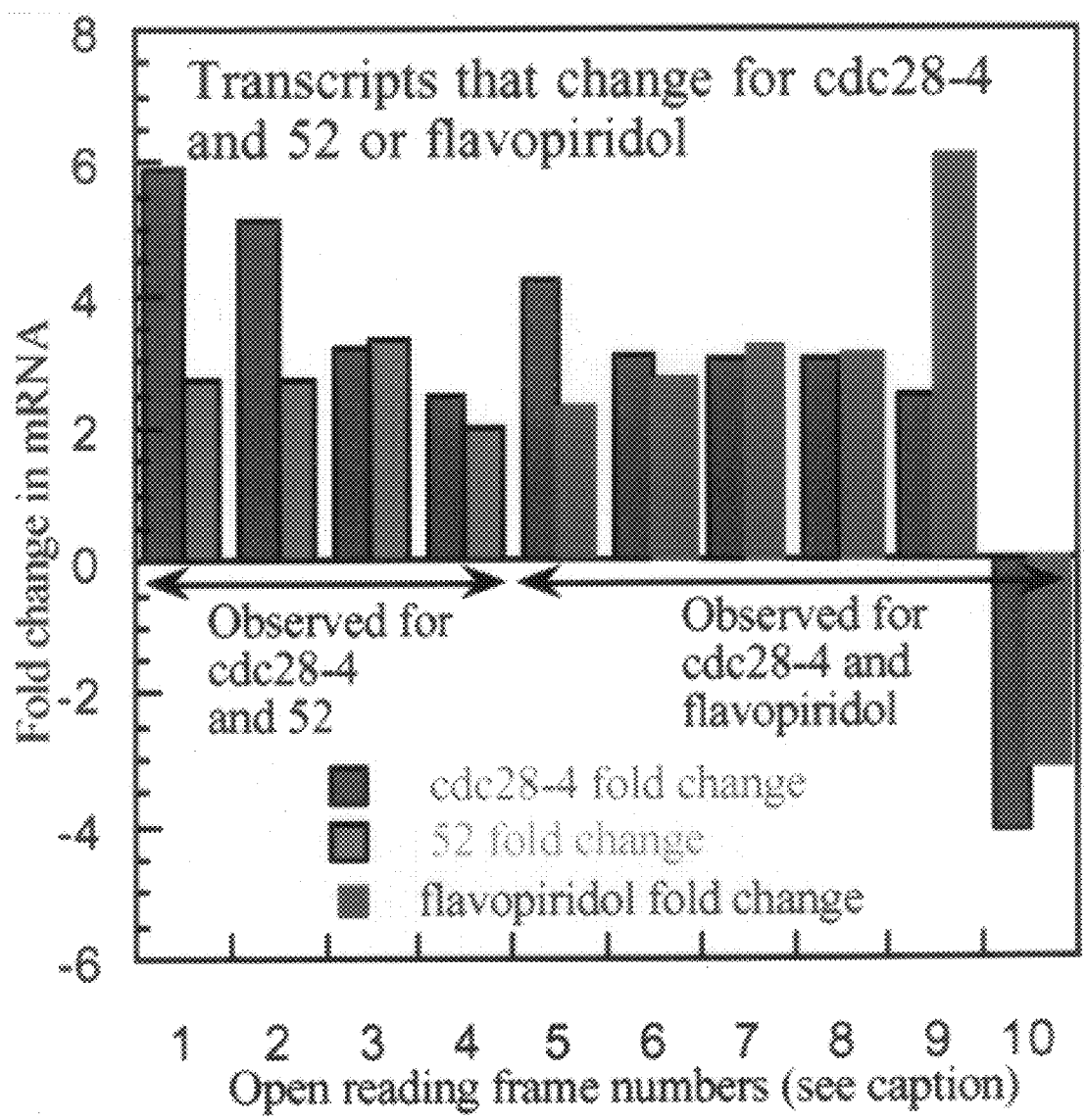
(FIG. 3B) Transcript changes that may result from Pho85p kinase inhibition observed in either the 52 or flavopiridol profiles: YOL001W (PHO80, a cyclin that associates with Pho85p); YGR233C (PHO81, inhibitory protein that associates with Pho80p or Pho85p); YFL014W (HSP12, heat shock protein); YHR071W (PCL5, cyclinlike and associates with Pho85p); YGR088W (CTT1, cytosolic catalase T); YBR093c (PHO5, secreted acid phosphatase); YLL039c (UBI4, ubiquitin); YCL009c (PHO84, phosphate transporter); YML116W(PHO8, vacuolar alkaline phosphatase); YBR296c (homologous to a phosphate-repressible permease).

Another set of genes that are clearly affected by both 52 and flavopiridol (but not by 52Me) are ones involved in phosphate metabolism, consistent with the observed in vitro inhibition of Pho85p (FIG. 3B). Intracellular phosphate levels in yeast are monitored by a system that relies on the Pho85p kinase complex to modulate the activity of a transcription factor or factors that regulate a variety of genes, including a secreted acid phosphatase (Pho5p) (24), genes involved in the stress response (the heat shock protein HSP12 and ubiquitin UBI4), and genes involved in glycogen metabolism. Proteins whose transcript levels were observed to increase for 52 or flavopiridol that are consistent with inhibition of the Pho85p kinase include Pho80p (whose transcription is known to be repressed by active Pho85), Pho81p (an endogenousPho85-Pho80 inhibitor), Pho84p (a phosphate permease), Pho5p, CTT1p, HSP12p, and UBI4 (25). Notably absent from this list is glycogen synthase (GSY2) (26), despite the large number of other glycogen metabolism mRNAs that change. Dissecting the transcriptional consequences of Pho85 inhibition (27) is additionally complicated because Pho85p associates with a large number of other cyclins (for example, Pcl1p–Pcl8p) (28) to yield complexes of unknown function that may also be subject to inhibition.

Compound 52 and flavopiridol also affect the transcript levels of many genes involved in cellular metabolism. For example, genes involved in glycolysis (PFK26 and YAL061W, an alcohol dehydrogenase), the citric acid cycle (ALD4), glycogen metabolism (PGM2 and YPR 84W, a putative debranching enzyme), gluconeogenesis (PCK1), and a probable sugar transporter (HXT), were induced. Other changes in transcript levels that were in common to both compounds and are likely to be associated with drug exposure include up-regulation of a number of genes encoding members of the ATP-binding cassette superfamily and other transport proteins (PDR10, PDR15), cell wall glycoproteins (YER150w), and cell wall proteins implicated in increased drug resistance (GSC2) (29); genes involved in vacuole endocytosis and regulation (YPT53, PMC1); and several heat shock genes (HSP26, HSP30, HSP82, HSP104, SSE2). Additional genes with changes in common to both compounds include a GTP- and ATP-binding protein (YDL223c) that putatively binds microtubules, 1-myo-inositol-1-phosphatesynthase (INO1), and 40 genes of unknown function. Very few of the 52 and flavopiridol-inducible genes were significantly induced by 52Me, suggesting that many of the drug-sensing mechanisms may respond to signals associated with the function rather than the structure of the drug.

Although Cdc28p is the intended target of both 52 and flavopiridol, more than half of the mRNA changes that result from exposure to the two compounds are distinct. For example, of the ~50 genes whose transcript levels were decreased at least threefold in response to 52, 14 were ribosomal proteins (including RPL4A, RPL26B, RPS24A). In contrast, no ribosomal protein transcript levels decreased more than threefold after treatment with flavopiridol. These results suggest that the two compounds may inhibit Cdc28p function (10) or affect pathways involving Cdc28p kinase activity to different degrees. Alternatively, the differential effects of the two compounds may result from different intracellular concentrations or from their effects on other cellular targets not specifically examined in vitro. Given the relatively large number of transcripts that are differentially affected by these two CDK inhibitors, we examined the transcriptional consequences of a genetic mutation in the Cdc28p kinase. Because CDC28 is an essential gene, the transcript profile of two cdc28 temperature-sensitive alleles [cdc28-4 and cdc28-13 (30)] and their isogenic wild-type strains were measured under permissive growth conditions (25° C.) in which the degree of growth inhibition approximates that observed at the concentrations used in the inhibitor profile experiments (31). The mutation leading to a reduction in Cdc28p kinase activity in the cdc28-4 mutant under permissive growth conditions (32) might be expected to simulate the effects of chemical inhibition.

Approximately 100 mRNAs in the cdc28-4 strain exhibited more than twofold inductions over the wild type (FIG. 3C). Only two of the cell cycle-associated genes (histones HTA1 and HTA2) that changed in response to flavopiridol or 52 were affected in this mutant (33). Instead, as with flavopiridol and 52, a number of metabolic genes involved in glycogen synthesis, the citric acid cycle, gluconeogenesis, and the glyoxylate cycle were induced (FIG. 3C). Consistent with these changes is the induction of the HAP4 transcription factor, which has been implicated in the regulation of many respiration genes (34).

Another class of transcripts induced in cdc28-4 were for genes involved in stress signaling (35), as well as heat shock elements, stress response elements, and members of the major facilitator superfamily. Other transcripts that were also affected by CDC28 mutation and in the small-molecule experiments include virtually all of the transcription factors and many of the metabolic, biosynthetic, and stress response genes as well as a set of unknown genes, some of which may be linked to cell cycle regulation. However, there were also a number of genes in these functional categories that showed significant changes only for the cdc28-4 mutant, including a protein with trans membrane domains (YOL155C), metabolic genes (ACH1), and a variety of proteins of unknown function. The transcriptional responses to this single point mutation in CDC28 can be interpreted as cellular responses that tend to mitigate the effects of this alteration. Complete inactivation of Cdc28p inase activity, rather than the partial inhibition at 25° C., may result in more cell cycle-related transcript changes. However, a host of additional changes associated with cell cycle arrest and secondary consequences of heat shock (required to induce arrest) are likely to appear as well, and these changes may complicate interpretation of the profile results.

Our current experimental design does not allow us to definitively identify the primary target or targets of inhibition by flavopiridol or 52. However, most of the genes that were commonly down-regulated by the two compounds are known to be involved in cell cycle progression and are affected in a way that is consistent with inhibition of Cdc28p activity. The transcript profiles also show distinct and reproducible differences in the effects of the two compounds despite their similar in vitro activity. Profiles of this sort may prove useful in evaluating the selectivity of drug candidates and in identifying proteins whose inhibition might specifically potentiate the effects of a primary drug. The lack of correspondence in the changes of mRNA transcript levels resulting from chemical and genetic inactivation underscores the intrinsic differences in these methods for modulating biological function.

Given the large number of purine-dependent cellular processes, purine libraries may serve as a rich source of inhibitors for many different protein targets. Indeed, purine analogs have been identified that selectively inhibit JNK kinase and glycogen synthasekinase (36, 37). By screening these libraries for their effects in whole-cell assays, it should be possible to search for compounds with a wide variety of activities (38). Both gene expression profiles and differential gene expression libraries should facilitate identification and characterization of targets (39). These and other approaches to generating selective inhibitors of different cellular processes should complement genetic methods in the study of cellular function.

Based on the results reported herein a number of different combination of oligonucleotide probes are determined to be useful for drug screening and identification purposes. Thus different combinations of probes can be used to test the effects that test compounds have on gene expression in cells. The cells may be mammalian, such as human or other eukaryote, such as yeast. Although yeast genes and cells are exemplified above, the human homologues are known in many cases. Because the functions of many of these genes are so essential for cells, they are believed to be extremely conserved among species, especially among eukaryotes.

The oligonucleotide probes can be used in any hybridization assay, solution or solid phase. Preferably the assays are done on a solid phase. More preferably the probes are bound to a solid support which is an array. Any number of probes can be used which specifically hybridize to genes which are affected by at least one of: compound 52, flavopiridol, and a cdc28-4 mutation. The direction of the effect may be either up- or down-regulation. The same direction of effect may be caused by all three agents, or any combination of ups and downs or no-effects.

As is known in the art, an oligonucleotide probe typically comprises at least 10 contiguous nucleotides of a gene sequence, and preferably 11, 13, 15, 17, 21, 25 or 30 nucleotides. Probes are desirably labeled with a moiety which is either radioactive, enzymatically detectable, antigenically detectable, or fluorometrically detectable.

The sets of probes of the present invention which detect genes which are regulated by compound 52, flavopiridol, or a cdc28-4 mutation may be present in larger groups of probes which are not so regulated. Preferably at least 10, 20, 40, 60, 80, 90 or 100% of the probes are those which are so regulated. The size of the sets of probes may vary greatly. The sets of probes may comprise at least 2, 3, 5, 7, 9, 11, 20, or 30 probes. They may comprise not more than 10, 20, 30, 100, 1000, or 10000. The upper and lower bounds of the set of probes are always chosen so that the set comprises at least 2 probes regulated as taught herein.

Drugs, according to the present invention, are any compounds which have an effect on a cell. The drug need not have any proven therapeutic benefit. They may be compounds being screened or further evaluated for their therapeutic benefits. The drugs may be small molecules, i.e., organic or inorganic chemicals. The drugs may be macromolecules or biologicals, such as antibodies, ligands, proteins, nucleic acids, antisense molecules, cytokines, chemokines, ribozynes, etc.

A set typically refers to an identified grouping of oligonucleotides that are put together in a common container or on a common object. These may be on an array or in a kit together. They are typically separated, either spatially on a solid support such as an array, or in separate vessels, such as vials or tubes. According to the present invention, at least 5% of the oligonucleotides or probes in a set are portions of genes which are up-regulated or down-regulated by compound 53, flavopiridol and/or a cdc28 mutant. Preferably more than 10%, 20%, 30%, 40%, 50%, 60%, 700%, 80%, 90%, or 95% of such oligonucleotides or probes in the set represent genes which are so regulated. Most preferably the genes are those identified in FIG. 3 or Table 3.

According to the present invention one can compare the specificity of drugs' effects by looking at the number of transcriptional targets which the drugs have and comparing them. More specific drugs will have less transcriptional targets. Similar sets of targets of two drugs indicates a similarity of effects. Transcriptional targets of a drug or drugs can be identified as a possible additional direct target for drug development. Similarly, the effects of mutations on transcriptional targets can be used to screen potential drugs. Drugs can be screened for the ability to simulate the transcriptional effects of mutations, to counteract the transcriptional effects of a mutation, or to augment the transcriptional effects of a mutation.

Comparison of patterns of transcription can be done by a human or by a computer. Transcription data (hybridization data) can be entered into the computer and the patterns can be compared. Both differences and similarities are useful to indicate specificities and downstream effected genes.

Downstream regulated genes of compound 52, flavopiridol, and cdc28 mutations, as identified herein, can be used in transcriptional screening methods as well as in protein screening methods. Imnological techniques can be used to assess the expression of the protein products of the identified genes. The products of the identified genes can be used directly in drug development programs to identify drugs which inhibit or stimulate the products.

I. Definitions

Bind(s) Substantially: "Bind(s) substantially" refers to complementary hybridization between a probe nucleic acid and a target nucleic acid and embraces minor mismatches that can be accommodated by reducing the stringency of the hybridization media to achieve the desired detection of the target polynucleotide sequence.

Backround: The terms "background" or "background signal intensity" refer to hybridization signals resulting from non-specific binding, or other interactions, between the labeled target nucleic acids and components of the oligonucleotide array (e.g., the oligonucleotide probes, control probes, the array substrate, etc.). Background signals may also be produced by intrinsic fluorescence of the array components themselves. A single background signal can be calculated for the entire array, or a different background signal may be calculated for each target nucleic acid. In a preferred embodiment, background is calculated as the average hybridization signal intensity for the lowest 5% to 10% of the probes in the array, or, where a different background signal is calculated for each target gene, for the lowest 5% to 10% of the probes for each gene. Of course, one of skill in the art will appreciate that where the probes to a particular gene hybridize well and thus appear to be specifically binding to a target sequence, they should not be used in a background signal calculation. Alternatively, background may be calculated as the average hybridization signal intensity produced by hybridization to probes that are not complementary to any sequence found in the sample (e.g. probes directed to nucleic acids of the opposite sense or to genes not found in the sample such as bacterial genes where the sample is mammalian nucleic acids). Background can also be calculated as the average signal intensity produced by regions of the array that lack any probes at all.

Hybridizing Specifically to: The phrase "hybridizing specifically to" refers to the binding, duplexing, or hybridizing of a molecule substantially to or only to a particular nucleotide sequence or sequences under stringent conditions when that sequence is present in a complex mixture (e.g., total cellular) DNA or RNA.

Introns: noncoding DNA sequences which separate neighboring coding regions. During gene transcription, introns, like exons, are transcribed into RNA but are subsequently removed by RNA splicing.

Massive Parallel Screening: The phrase "massively parallel screening" refers to the simultaneous screening of at least about 100, preferably about 1000, more preferably about 10,000 and most preferably about 1,000,000 different nucleic acid hybridizations.

Mismatch Control: The term "mismatch control" or "mismatch probe" refer to a probe whose sequence is deliberately selected not to be perfectly complementary to a particular target sequence. For each mismatch (MM) control in a high-density array there typically exists a corresponding perfect match (PM) probe that is perfectly complementary to the same particular target sequence. The mismatch may comprise one or more bases. While the mismatch(es) may be located anywhere in the mismatch probe, terminal mismatches are less desirable as a terminal mismatch is less likely to prevent hybridization of the target sequence. In a particularly preferred embodiment, the mismatch is located at or near the center of the probe such that the mismatch is most likely to destabilize the duplex with the target sequence under the test hybridization conditions.

mRNA or Transcript: The term "mRNA" refers to transcripts of a gene. Transcripts are RNA including, for example, mature messenger RNA ready for translation, products of various stages of transcript processing. Transcript processing may include splicing, editing and degradation.

Nucleic Acid: The terms "nucleic acid" or "nucleic acid molecule" refer to a deoxyribonucleotide or ribonucleotide polymer in either single-or double-stranded form, and unless otherwise limited, would encompass analogs of natural nucleotide that can function in a similar manner as naturally occurring nucleotide. A n oligo-nucleotide is a single-stranded nucleic acid of 2 to n bases, where n may be greater than 500 to 1000. Nucleic acids may be cloned or synthesized using any technique known in the art. They may also include non-natually occurring nucleotide analogs, such as those which are modified to improve hybridization and peptide nucleic acids.

Nucleic Acid Encoding a Regulatory Molecule: The regulatory molecule may be DNA, RNA or protein. Thus for example DNA sites which bind protein or other nucleic acid molecules are included within the class of regulatory molecules encoded by a nucleic acid.

Perfect Match Probe: The term "perfect match probe" refers to a probe that has a sequence that is perfectly complementary to a particular target sequence. The test probe is typically perfectly complementary to a portion (subsequence) of the target sequence. The perfect match (PM) probe can be a "test probe", a "normalization control" probe, an expression level control probe and the like. A perfect match control or perfect match probe is, however, distinguished from a "mismatch control" or "mismatch probe."

Probe: As used herein a "probe" is defined as a nucleic acid, capable of binding to a target nucleic acid of complementary sequence through one or more types of chemical bonds, usually through complementary base pairing, usually through hydrogen bond formation. As used herein, a probe may include natural (i.e. A, G, U, C, or T) or modified bases (7-deazaguanosine, inosine, etc.). In addition, the bases in probes may be joined by a linkage other than a phosphodiester bond, so long as it does not interfere with hybridization. Thus, probes may be peptide nucleic acids in which the constituent bases are joined by peptide bonds rather than phosphodiester linkages.

Target Nucleic Acid: The term "target nucleic acid" refers to a nucleic acid (often derived from a biological sample), to which the probe is designed to specifically hybridize. It is either the presence or absence of the target nucleic acid that is to be detected, or the amount of the target nucleic acid that is to be quantified. The target nucleic acid has a sequence that is complementary to the nucleic acid sequence of the corresponding probe directed to the target. The term target nucleic acid may refer to the specific subsequence of a larger nucleic acid to which the probe is directed or to the overall sequence (e.g., gene or mRNA) whose expression level it is desired to detect. The difference in usage will be apparent from context.

Stringent Conditions: The term "stringent conditions" refers to conditions under which a probe will hybridize to its target subsequence, but with only insubstantial hybridization to other sequences or to other sequences such that the difference may be identified. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH.

Subsequence: "Subsequence" refers to a sequence of nucleic acids that comprise a part of a longer sequence of nucleic acids.

Thermal Melting Point (Tm): The Tm is the temperature, under defined ionic strength, pH, and nucleic acid concentration, at which 50% of the probes complementary to the target sequence hybridize to the target sequence at equilibrium. As the target sequences are generally present in excess, at Tm, 50% of the probes are occupied at equilibrium). Typically, stringent conditions will be those in which the salt concentration is at least about 0.01 to 1.0 M Na ion concentration (or other salts) at pH 7.0 to 8.3 and the temperature is at least about 30 C for short probes (e.g., 10 to 50 nucleotide). Stringent conditions may also be achieved with the addition of destabilizing agents such as formamide.

Quantifying: The term "quantifying" when used in the context of quantifying transcription levels of a gene can refer to absolute or to relative quantification. Absolute quantification may be accomplished by inclusion of known concentration(s) of one or more target nucleic acids (e.g. control nucleic acids such as Bio B or with known amounts the target nucleic acids themselves) and referencing the hybridization intensity of unknowns with the known target nucleic acids (e.g. through generation of a standard curve). Alternatively, relative quantification can be accomplished by comparison of hybridization signals between two or more genes, or between two or more treatments to quantify the changes in hybridization intensity and, by implication, transcription level.

Sequence Identity: The "percentage of sequence identity" or "sequence identity" is determined by comparing two optimally aligned sequences or subsequences over a comparison window or span, wherein the portion of the polynucleotide sequence in the comparison window may optionally comprise additions or deletions (i.e., gaps) as compared to the reference sequence (which does not comprise additions or deletions) for optimal alignment of the two sequences. The percentage is calculated by determining the number of positions at which the identical subunit (e.g. nucleic acid base or amino acid residue) occurs in both sequences to yield the number of matched positions, dividing the number of matched positions by the total number of positions in the window of comparison and multiplying the result by 100 to yield the percentage of sequence identity. Percentage sequence identity when calculated using the programs GAP or BESTFIT (see below) is calculated using default gap weights.

Methods of alignment of sequences for comparison are well known in the art. Optimal alignment of sequences for comparison may be conducted by the local homology algorithm of Smith and Waterman, *Adv. Appl. Math.* 2: 482 (1981), by the homology alignment algorithm of Needleman and Wunsch *J Mol Biol.* 48: 443 (1970), by the search for similarity method of Pearson and Lipman, *Proc. Natl Acad. Sci. USA* 85: 2444 (1988), by computerized implementations of these algorithms (including, but not limited to CLUSTAL in the PC/Gene program by Intelligenetics, Moutain View, Calif., GAP, BESTFIT, FASTA, and TFASTA in the Wis. Genetics Software Package, Genetics Computer Group (GCG), 575 Science Dr., Madison, Wis., USA), or by inspection. In particular, methods for aligning sequences using the CLUSTAL program are well described by Higgins and Sharp in *Gene*, 73: 237–244 (1988) and in *CABIOS* 5: 151–153 (1989)).

This invention provides methods and compositions for interrogating the genetic network and for studying the influence on expression of candidate drugs and mutations. The methods involve quantifying the level of expression of a large number of genes. In some preferred embodiments, a high density oligonucleotide array is used to hybridize with a target nucleic acid sample to detect the expression level of a large number of genes, preferably more than 10, more preferably more than 100, and most preferably more than 1000 genes.

Activity of a gene is reflected by the activity of its product(s): the proteins or other molecules encoded by the gene. Those product molecules perform biological functions. Directly measuring the activity of a gene product is, however, often difficult for certain genes. Instead, the immunological activities or the amount of the final product(s) or its peptide processing intermediates are determined as a measurement of the gene activity. More frequently, the amount or activity of intermediates, such as transcripts, RNA processing intermediates, or mature mRNAs are detected as a measurement of gene activity.

In many cases, the form and function of the final product (s) of a gene is unknown. In those cases, the activity of a gene is measured conveniently by the amount or activity of transcript(s), RNA processing intermediate(s), mature mRNA(s) or its protein product(s) or functional activity of its protein product(s).

Any methods that measure the activity of a gene are useful for at least some embodiments of this invention. For example, traditional Northern blotting and hybridization, nuclease protection, RT-PCR and differential display have been used for detecting gene activity. Those methods are useful for some embodiments of the invention. However, this invention is most useful in conjunction with methods for detecting the expression of a large number of genes.

High density arrays are particularly useful for monitoring the expression control at the transcriptional, RNA processing and degradation level. The fabrication and application of high density arrays in gene expression monitoring have been disclosed previously in, for example, WO 97/10365, WO 92/10588, U.S. application Ser. No. 08/772,376 filed Dec. 23, 1996; Ser. No. 08/529,115 filed on Sep. 15, 1995; Ser. No. 08/168,904 filed Dec. 15, 1993; Ser. No. 07/624,114 filed on Dec. 6, 1990, Ser. No. 07/362,901 filed Jun. 7, 1990, all incorporated herein for all purposed by reference. In some embodiment using high density arrays, high density oligonucleotide arrays are synthesized using methods such as the Very Large Scale Immobilized Polymer Synthesis (VLSIPS) disclosed in U.S. Pat. No. 5,445,934 incorporated herein for all purposes by reference. Each oligonucleotide occupies a known location on a substrate. A nucleic acid target sample is hybridized with a high density array of oligonucleotides and then the amount of target nucleic acids hybridized to each probe in the array is quantified. One preferred quantifying method is to use confocal microscope and fluorescent labels. The GeneChip® system (Affymetrix, Santa Clara, Calif.) is particularly suitable for quantifying the hybridization; however, it will be apparent to those of skill in the art that any similar systems or other effectively equivalent detection methods can also be used.

High density arrays are suitable for quantifying a small variations in expression levels of a gene in the presence of a large population of heterogeneous nucleic acids. Such high density arrays can be fabricated either by de novo synthesis on a substrate or by spotting or transporting nucleic acid sequences onto specific locations of substrate. Nucleic acids are purified and/or isolated from biological materials, such as a bacterial plasmid containing a cloned segment of sequence of interest. Suitable nucleic acids are also produced by amplification of templates. As a nonlimiting illustration, polymerase chain reaction, and/or in vitro transcription, are suitable nucleic acid amplification methods.

Synthesized oligonucleotide arrays are particularly preferred for this invention. Oligonucleotide arrays have numerous advantages, as opposed to other methods, such as efficiency of production, reduced intra- and inter array variability, increased information content and high signal-to-noise ratio.

Preferred high density arrays for gene function identification and genetic network mapping comprise greater than about 100, preferably greater than about 1000, more preferably greater than about 16,000 and most preferably greater than 65,000 or 250,000 or even greater than about 1,000,000 different oligonucleotide probes, preferably in less than 1 $cm^2$ of surface area. The oligonucleotide probes range from about 5 to about 50 or about 500 nucleotides, more preferably from about 10 to about 40 nucleotide and most preferably from about 15 to about 40 nucleotides in length.

Massive Parallel Gene Expression Monitoring

One preferred method for massive parallel gene expression monitoring is based upon high density nucleic acid arrays. Nucleic acid array methods for monitoring gene expression are disclosed and discussed in detail in PCT Application WO 092.10588 (published on Jun. 25, 1992), all incorporated herein by reference for all purposes.

Generally those methods of monitoring gene expression involve (a) providing a pool of target nucleic acids comprising RNA transcript(s) of one or more target gene(s), or nucleic acids derived from the RNA transcript(s); (b) hybridizing the nucleic acid sample to a high density array of probes and (c) detecting the hybridized nucleic acids and calculating a relative and/or absolute expression (transcription, RNA processing or degradation) level.

(A) Providing a Nucleic Acid Sample

One of skill in the art will appreciate that it is desirable to have nucleic samples containing target nucleic acid sequences that reflect the transcripts of interest. Therefore, suitable nucleic acid samples may contain transcripts of interest. Suitable nucleic acid samples, however, may contain nucleic acids derived from the transcripts of interest. As used herein, a nucleic acid derived from a transcript refers to a nucleic acid for whose synthesis the mRNA transcript or a subsequence thereof has ultimately served as a template. Thus, a cDNA reverse transcribed from a transcript, an RNA transcribed from that cDNA, a DNA amplified from the cDNA, an RNA transcribed from the amplified DNA, etc., are all derived from the transcript and detection of such derived products is indicative of the presence and/or abundance of the original transcript in a sample. Thus, suitable samples include, but are not limited to, transcripts of the gene or genes, cDNA reverse transcribed from the transcript, cRNA transcribed from the cDNA, DNA amplified from the genes, RNA transcribed from amplified DNA, and the like.

Transcripts, as used herein, may include, but not limited to pre-mRNA nascent transcript(s), transcript processing intermediates, mature mRNA(s) and degradation products. It is not necessary to monitor all types of transcripts to practice this invention. For example, one may choose to practice the invention to measure the mature mRNA levels only.

In one embodiment, such sample is a homogenate of cells or tissues or other biological samples. Preferably, such sample is a total RNA preparation of a biological sample. More preferably in some embodiments, such a nucleic acid sample is the total mRNA isolated from a biological sample. Those of skill in the art will appreciate that the total mRNA prepared with most methods includes not only the mature mRNA, but also the RNA processing intermediates and nascent pre-mRNA transcripts. For example, total mRNA purified with a poly (dT) column contains RNA molecules with poly (A) tails. Those polyA$^+$ RNA molecules could be mature mRNA, RNA processing intermediates, nascent transcripts or degradation intermediates.

Biological samples may be of any biological tissue or fluid or cells from any organism. Frequently the sample will be a "clinical sample" which is a sample derived from a patient. Clinical samples provide a rich source of information regarding the various states of genetic network or gene expression. Some embodiments of the invention are employed to detect mutations and to identify the phenotype of mutations. Such embodiments have extensive applications in clinical diagnostics and clinical studies. Typical clinical samples include, but are not limited to, sputum, blood, blood cells (e.g., white cells), tissue or fine needle biopsy samples, urine, peritoneal fluid, and pleural fluid, or cells therefrom. Biological samples may also include sections of tissues, such as frozen sections or formalin fixed sections taken for histological purposes.

Another typical source of biological samples are cell cultures where gene expression states can be manipulated to explore the relationship among genes. In one aspect of the invention, methods are provided to generate biological samples reflecting a wide variety of states of the genetic network.

One of skill in the art would appreciate that it is desirable to inhibit or destroy RNase present in homogenates before homogenates can be used for hybridization. Methods of inhibiting or destroying nucleases are well known in the art. In some preferred embodiments, cells or tissues are homogenized in the presence of chaotropic agents to inhibit nuclease. In some other embodiments, RNase is inhibited or destroyed by heat treatment followed by proteinase treatment.

Methods of isolating total mRNA are also well known to those of skill in the art. For example, methods of isolation and purification of nucleic acids are described in detail in Chapter 3 of *Laboratory Techniques in Biochemistry and Molecular Biology: Hybridization With Nucleic Acid Probes, Part I. Theory and Nucleic Acid Preparation*, P. Tijssen, ed. Elsevier, N.Y. (1993) and Chapter 3 of *Laboratory Techniques in Biochemistry and Molecular Biology: Hybridization With Nucleic Acid Probes, Part I. Theory and Nucleic Acid Preparation*, P. Tijssen, ed. Elsevier, N.Y. (1993)).

In a preferred embodiment, the total RNA is isolated from a given sample using, for example, an acid guanidinium-phenol-chloroform extraction method and polyA$^+$ mRNA is isolated by oligo(dT) column chromatography or by using (dT) on magnetic beads (see, e.g., Sambrook et al., *Molecular Cloning: A Laboratory Manual* (2nd ed.), Vols. 1–3, Cold Spring Harbor Laboratory, (1989), or *Current Protocols in Molecular Biology*, F. Ausubel et al, ed. Greene Publishing and Wiley-Interscience, New York (1987)).

Frequently, it is desirable to amplify the nucleic acid sample prior to hybridization. One of skill in the art will appreciate that whatever amplification method is used, if a quantitative result is desired, care must be taken to use a method that maintains or controls for the relative frequencies of the amplified nucleic acids to achieve quantitative amplification.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. The high density array may then include probes specific to the internal standard for quantification of the amplified nucleic acid.

One preferred internal standard is a synthetic AW106 cRNA. The AW106 cRNA is combined with RNA isolated from the sample according to standard techniques known to those of skilled in the art. The RNA is then reverse transcribed using a reverse transcriptase to provide copy DNA The cDNA sequences are then amplified (e.g., by PCR) using labeled primers. The amplification products are separated, typically by electrophoresis, and the amount of radioactivity (proportional to the amount of amplified product) is determined. The amount of mRNA in the sample is then calculated by comparison with the signal produced by the known AW106 RNA standard. Detailed protocols for quantitative PCR are provided in *PCR Protocols, A Guide to Methods and Applications*, Innis et al., Academic Press, Inc. N.Y., (1990).

Other suitable amplification methods include, but are not limited to polymerase chain reaction (PCR) (Innis, et al., *PCR Protocols. A guide to Methods and Application*. Academic Press, Inc. San Diego, (1990)), ligase chain reaction (LCR) (see Wu and Wallace, *Genomics*, 4: 560 (1989), Landegren, et al., *Science*, 241: 1077 (1988) and Barringer, et al., *Gene*, 89: 117 (1990), transcription amplification (Kwoh, et al., *Proc. Natl Acad Sci. USA*, 86: 1173 (1989)), and self-sustained sequence replication (Guatelli, et al, *Proc. Nat Acad Sci. USA*, 87: 1874 (1990)).

Cell lysates or tissue homogenates often contain a number of inhibitors of polymerase activity. Therefore, RT-PCR typically incorporates preliminary steps to isolate total RNA or mRNA for subsequent use as an amplification template. A one-tube mRNA capture method may be used to prepare poly(A)$^+$ RNA samples suitable for immediate RT-PCR in the same tube (Boehringer Mannheim). The captured mRNA can be directly subjected to RT-PCR by adding a reverse transcription mix and, subsequently, a PCR mix.

In a particularly preferred embodiment, the sample mRNA is reverse transcribed with a reverse transcriptase and a primer consisting of oligo(dT) and a sequence encoding the phage T7 promoter to provide single stranded DNA template. The second DNA strand is polymerized using a DNA polymerase. After synthesis of double-stranded cDNA, T7 RNA polymerase is added and RNA is transcribed from the cDNA template. Successive rounds of transcription from each single cDNA template results in amplified RNA. Methods of in vitro polymerization are well known to those of skill in the art (see, e.g. Sambrook, supra) and this particular method is described in detail by Van Gelder, et al., *Proc. Natl Acad. Sci. USA*, 87: 1663–1667 (1990) who demonstrate that in vitro amplification according to this method preserves the relative frequencies of the various RNA transcripts. Moreover, Eberwine et al. *Proc. Natl Acad Sci. USA*, 89: 3010–3014 provide a protocol that uses two rounds of amplification via in vitro transcription to achieve greater than $10^6$ fold amplification of the original starting material, thereby permitting expression monitoring even where biological samples are limited.

It will be appreciated by one of skill in the art that the direct transcription method described above provides an antisense (aRNA) pool. Where antisense RNA is used as the target nucleic acid, the oligonucleotide probes provided in the array are chosen to be complementary to subsequences of the antisense nucleic acids. Conversely, where the target nucleic acid pool is a pool of sense nucleic acids, the oligonucleotide probes are selected to be complementary to subsequences of the sense nucleic acids. Finally, where the nucleic acid pool is double stranded, the probes may be of either sense as the target nucleic acids include both sense and antisense strands.

The protocols cited above include methods of generating pools of either sense or antisense nucleic acids. Indeed, one approach can be used to generate either sense or antisense nucleic acids as desired. For example, the cDNA can be directionally cloned into a vector (e.g., Stratagene's p Bluscript II KS (+) phagemid) such that it is flanked by the T3 and T7 promoters. In vitro transcription with the T3 polymerase will produce RNA of one sense (the sense depending on the orientation of the insert), while in vitro transcription with the T7 polymerase will produce RNA having the opposite sense. Other suitable cloning systems include phage lambda vectors designed for Cre-loxP plasnid subcloning (see e.g. Palazzolo et al., *Gene*, 88: 25–36 (1990)).

(B) Hybridizing Nucleic Acids to High Density Arrays

1. Probe Design

One of skill in the art will appreciate that an enormous number of array designs are suitable for the practice of this invention. The high density array will typically include a number of probes that specifically hybridize to the sequences of interest. In addition, in a preferred embodiment, the array will include one or more control probes.

The high density array chip includes "test probes." Test probes could be oligonucleotides that range from about 5 to about 45 or 5 to about 500 nucleotides, more preferably from about 10 to about 40 nucleotides and most preferably from about 15 to about 40 nucleotides in length. In other particularly preferred embodiments the probes are 20 or 25 nucleotides in length. In another preferred embodiments, test probes are double or single strand DNA sequences. DNA sequences are isolated or cloned from nature sources or amplified from nature sources using nature nucleic acid as templates. These probes have sequences complementary to particular subsequences of the genes whose expression they are designed to detect. Thus, the test probes are capable of specifically hybridizing to the target nucleic acid they are to detect.

In addition to test probes that bind the target nucleic acid(s) of interest, the high density array can contain a number of control probes. The control probes fall into three categories referred to herein as 1) normalization controls; 2) expression level controls; and 3) mismatch controls.

Normalization controls are oligonucleotide or other nucleic acid probes that are complementary to labeled reference oligonucleotides or other nucleic acid sequences that are added to the nucleic acid sample. The signals obtained from the normalization controls after hybridization provide a control for variations in hybridization conditions, label intensity, "reading" efficiency and other factors that may cause the signal of a perfect hybridization to vary between arrays. In a preferred embodiment, signals (e.g., fluorescence intensity) read from all other probes in the array are divided by the signal (e.g., fluorescence intensity) from the control probes thereby normalizing the measurements.

Virtually any probe may serve as a normalization control. However, it is recognized that hybridization efficiency varies with base composition and probe length Preferred normalization probes are selected to reflect the average length of the other probes present in the array, however, they can be selected to cover a range of lengths. The normalization control(s) can also be selected to reflect the (average) base composition of the other probes in the array, however in a preferred embodiment, only one or a few normalization probes are used and they are selected such that they hybridize well (i.e. no secondary structure) and do not match any target-specific probes.

Expression level controls are probes that hybridize specifically with constitutively expressed genes in the biological sample. Virtually any constitutively expressed gene provides a suitable target for expression level controls. Typically expression level control probes have sequences complementary to subsequences of constitutively expressed "housekeeping genes" including, but not limited to the β-actin gene, the transferrin receptor gene, the GAPDH gene, and the like.

Mismatch controls may also be provided for the probes to the target genes, for expression level controls or for normalization controls. Mismatch controls are oligonucleotide probes or other nucleic acid probes identical to their corresponding test or control probes except for the presence of one or more mismatched bases. A mismatched base is a base selected so that it is not complementary to the corresponding base in the target sequence to which the probe would otherwise specifically hybridize. One or more mismatches are selected such that under appropriate hybridization conditions (e.g. stringent conditions) the test or control probe would be expected to hybridize with its target sequence, but the mismatch probe would not hybridize (or would hybridize to a significantly lesser extent). Preferred mismatch probes contain a central mismatch. Thus, for example, where a probe is a 20mer, a corresponding mismatch probe will have the identical sequence except for a single base mismatch (e.g., substituting a G, a C or a T for an A) at any of positions 6 through 14 (the central mismatch).

Mismatch probes thus provide a control for non-specific binding or cross-hybridization to a nucleic acid in the sample other than the target to which the probe is directed. Mismatch probes thus indicate whether a hybridization is specific or not. For example, if the target is present the perfect match probes should be consistently brighter than the mismatch probes. In addition, if all central mismatches are present, the mismatch probes can be used to detect a mutation. The difference in intensity between the perfect match and the mismatch probe (I(PM)-I(MM)) provides a good measure of the concentration of the hybridized material.

The high density array may also include sample preparation/amplification control probes. These are probes that are complementary to subsequences of control genes selected because they do not normally occur in the nucleic acids of the particular biological sample being assayed. Suitable sample preparation/amplification control probes include, for example, probes to bacterial genes (e.g., Bio B) where the sample in question is a biological from a eukaryote.

The RNA sample is then spiked with a known amount of the nucleic acid to which the sample preparation/amplification control probe is directed before processing. Quantification of the hybridization of the sample preparation/amplification control probe then provides a measure of alteration in the abundance of the nucleic acids caused by processing steps (e.g. PCR, reverse transcription, in vitro transcription, etc.).

In a preferred embodiment, oligonucleotide probes in the high density array are selected to bind specifically to the nucleic acid target to which they are directed with minimal non-specific binding or cross-hybridization under the particular hybridization conditions utilized. Because the high density arrays of this invention can contain in excess of 1,000,000 different probes, it is possible to provide every probe of a characteristic length that binds to a particular nucleic acid sequence. Thus, for example, the high density array can contain every possible 20-mer sequence complementary to an IL-2 mRNA.

However, there may exist 20-mer subsequences that are not unique to the IL-2 mRNA Probes directed to these subsequences are expected to cross-hybridize with occurrences of their complementary sequence in other regions of the sample genome. Similarly, other probes simply may not hybridize effectively under the hybridization conditions (e.g., due to secondary structure, or interactions with the substrate or other probes). Thus, in a preferred embodiment, the probes that show such poor specificity or hybridization efficiency are identified and may not be included either in the high density array itself (e.g., during fabrication of the array) or in the post-hybridization data analysis.

In addition, in a preferred embodiment, expression monitoring arrays are used to identify the presence and expression (transcription) level of genes which are several hundred base pairs long For most applications it would be useful to identify the presence, absence, or expression level of several thousand to one hundred thousand genes. Because the number of oligonucleotides per array is limited in a preferred embodiment, it is desired to include only a limited set of probes specific to each gene whose expression is to be detected.

As disclosed in U.S. application Ser. No. 08/772,376, probes as short as 15, 20, or 25 nucleotide are sufficient to hybridize to a subsequence of a gene and that, for most genes, there is a set of probes that performs well across a wide range of target nucleic acid concentrations. In a preferred embodiment, it is desirable to choose a preferred or "optimum" subset of probes for each gene before synthesizing the high density array.

2. Forming High Density Arrays.

Methods of forming high density arrays of oligonucleotides, peptides and other polymer sequences with a minimal number of synthetic steps are known. The oligonucleotide analogue array can be synthesized on a solid substrate by a variety of methods, including, but not limited to, light-directed chemical coupling, and mechanically directed coupling See Pirrung et al, U.S. Pat. No. 5,143,854 (see also PCT Application No. WO 90/15070) and Fodor et al., PCT Publication Nos. WO 92/10092 and WO 93/09668 and U.S. Ser. No. 07/980,523 which disclose methods of forming vast arrays of peptides, oligonucleotides and other molecules using, for example, light-directed synthesis techniques. See also, Fodor et al., *Science*, 251, 767–77 (1991). These procedures for synthesis of polymer arrays are now referred to as VLSIPS™ procedures. Using the VLSIPS™ approach, one heterogeneous array of polymers is converted, through simultaneous coupling at a number of reaction sites, into a different heterogeneous array. See, U.S. application Ser. Nos. 07/796,243 and 07/980,523.

The development of VLSIPS™ technology as described in the above-noted U.S. Pat. No. 5,143,854 and PCT patent publication Nos. WO 90/15070 and 92/10092, is considered pioneering technology in the fields of combinatorial synthesis and screening of combinatorial libraries. More recently, patent application Ser. No. 08/082,937, fled Jun. 25, 1993, describes methods for making arrays of oligonucleotide probes that can be used to check or determine a partial or complete sequence of a target nucleic acid and to detect the presence of a nucleic acid containing a specific oligonucleotide sequence.

In brief the light-directed combinatorial synthesis of oligonucleotide arrays on a glass surface proceeds using automated phosphoramidite chemistry and chip masking techniques. In one specific implementation, a glass surface is derivatized with a silane reagent containing a functional group, e.g., a hydroxyl or amine group blocked by a photolabile protecting group. Photolysis through a photolithogaphic mask is used selectively to expose functional groups which are then ready to react with incoming 5'-photoprotected nucleoside phosphoramidites. The phosphoramidites react only with those sites which are illuminated (and thus exposed by removal of the photolabile blocking group). Thus, the phosphoramidites only add to those areas selectively exposed from the preceding step. These steps are repeated until the desired array of sequences have been synthesized on the solid surface. Combinatorial synthesis of different oligonucleotide analogues at different locations on the array is determined by the pattern of illumination during synthesis and the order of addition of coupling reagents.

In the event that an oligonucleotide analogue with a polyamide backbone is used in the VLSIPS™ procedure, it is generally inappropriate to use phosphoramidite chemistry to perform the synthetic steps, since the monomers do not attach to one another via a phosphate linkage. Instead, peptide synthetic methods are substituted. See, e.g., Pirrung et al. U.S. Pat. No. 5,143,854.

Peptide nucleic acids are commercially available from, e.g., Biosearch, Inc. (Bedford, Mass.) which comprise a polyamide backbone and the bases found in naturally occurring nucleosides. Peptide nucleic acids are capable of binding to nucleic acids with high specificity, and are considered "oligonucleotide analogues" for purposes of this disclosure.

In addition to the foregoing, additional methods which can be used to generate an array of oligonucleotides on a single substrate are described in co-pending applications Ser. No. 07/980,523, filed Nov. 20, 1992, and 07/796,243, filed Nov. 22, 1991 and in PCT Publication No. WO 93/09668. In the methods disclosed in these applications, reagents are delivered to the substrate by either (1) flowing within a channel defined on predefined regions or (2) "spotting" on predefined regions or (3) through the use of photoresist. However, other approaches, as well as combinations of spotting and flowing, may be employed. In each instance, certain activated regions of the substrate are mechanically separated from other regions when the monomer solutions are delivered to the various reaction sites.

A typical "flow channel" method applied to the compounds and libraries of the present invention can generally be described as follows. Diverse polymer sequences are synthesized at selected regions of a substrate or solid support by forming flow channels on a surface of the substrate through which appropriate reagents flow or in which appropriate reagents are placed. For example, assume a monomer "A" is to be bound to the substrate in a first group of selected regions. If necessary, all or part of the surface of the substrate in all or a part of the selected regions is activated for binding by, for example, flowing appropriate reagents through all or some of the channels, or by washing the entire substrate with appropriate reagents. After placement of a channel block on the surface of the substrate, a reagent having the monomer A flows through or is placed in all or some of the channel(s). The channels provide fluid contact to the first selected regions, thereby binding the monomer A on the substrate directly or indirectly (via a spacer) in the first selected regions.

Thereafter, a monomer B is coupled to second selected regions, some of which may be included among the first selected regions. The second selected regions will be in fluid contact with a second flow channel(s) through translation, rotation, or replacement of the channel block on the surface of the substrate; through opening or closing a selected valve; or through deposition of a layer of chemical or photoresist. If necessary, a step is performed for activating at least the second regions. Thereafter, the monomer B is flowed through or placed in the second flow channel(s), binding monomer B at the second selected locations. In this particular example, the resulting sequences bound to the substrate at this stage of processing will be, for example, A, B, and AB. The process is repeated to form a vast array of sequences of desired length at known locations on the substrate.

After the substrate is activated, monomer A can be flowed through some of the channels, monomer B can be flowed through other channels, a monomer C can be flowed through still other channels, etc. In this manner, many or all of the reaction regions are reacted with a monomer before the channel block must be moved or the substrate must be washed and/or reactivated. By making use of many or all of the available reaction regions simultaneously, the number of washing and activation steps can be minimized.

One of skill in the art will recognize that there are alternative methods of forming channels or otherwise protecting a portion of the surface of the substrate. For example, according to some embodiments, a protective coating such as a hydrophilic or hydrophobic coating (depending upon the nature of the solvent) is utilized over portions of the substrate to be protected, sometimes in combination with materials that facilitate wetting by the reactant solution in other regions. In this manner, the flowing solutions are further prevented from passing outside of their designated flow paths.

High density nucleic acid arrays can be fabricated by depositing presynthezied or natural nucleic acids in predined positions. Synthesized or natural nucleic acids are deposited on specific locations of a substrate by light directed targeting and oligonucleotide directed targeting. Nucleic acids can also be directed to specific locations in much the same manner as the flow channel methods. For example, a nucleic acid A can be delivered to and coupled with a first group of reaction regions which have been appropriately activated. Thereafter, a nucleic acid B can be delivered to and reacted with a second group of activated reaction regions. Nucleic acids are deposited in selected regions. Another embodiment uses a dispenser that moves from region to region to deposit nucleic acids in specific spots. Typical dispensers include a micropipette or capillary pin to deliver nucleic acid to the substrate and a robotic system to control the position of the micropipette with respect to the substrate. In other embodiments, the dispenser includes a series of tubes, a manifold, an array of pipettes or capillary pins, or the like so that various reagents can be delivered to the reaction regions simultaneously.

3. Hybridization

Nucleic acid hybridization simply involves contacting a probe and target nucleic acid under conditions where the probe and its complementary target can form stable hybrid duplexes through complementary base pairing. The nucleic acids that do not form hybrid duplexes are then washed away leaving the hybridized nucleic acids to be detected, typically through detection of an attached detectable label. It is generally recognized that nucleic acids are denatured by increasing the temperature or decreasing the salt concentration of the buffer containing the nucleic acids. Under low stringency conditions (e.g., low temperature and/or high salt) hybrid duplexes (e.g., DNA:DNA, RNA:RNA, or RNA:DNA) will form even where the annealed sequences are not perfectly complementary. Thus specificity of hybridization is reduced at lower stringency. Conversely, at higher stringency (e.g., higher temperature or lower salt) successful hybridization requires fewer mismatches.

One of skill in the art will appreciate that hybridization conditions may be selected to provide any degree of stringency. In a preferred embodiment, hybridization is performed at low stringency in this case in 6×SSPE-T at 37 C (0.005% Triton X-100) to ensure hybridization and then subsequent washes are performed at higher stringency (e.g., 1×SSPE-T at 37 C) to eliminate mismatched hybrid duplexes. Successive washes may be performed at increasingly higher stringency (e.g., down to as low as 0.25× SSPE-T at 37 C to 50 C) until a desired level of hybridization specificity is obtained. Stringency can also be increased by addition of agents such as formamide. Hybridization specificity may be evaluated by comparison of hybridization to the test probes with hybridization to the various controls that can be present (e.g., expression level control, normalization control, mismatch controls, etc.).

In general there is a tradeoff between hybridization specificity (stringency) and signal intensity. Thus, in a preferred embodiment, the wash is performed at the highest stringency that produces consistent results and that provides a signal intensity greater than approximately 10% of the background intensity. Thus, in a preferred embodiment, the hybridized array may be washed at successively higher stringency solutions and read between each wash. Analysis of the data sets thus produced will reveal a wash stringency above which the hybridization pattern is not appreciably altered and which provides adequate signal for the particular oligonucleotide probes of interest.

In a preferred embodiment, background signal is reduced by the use of a detergent (e.g, C-TAB) or a blocking reagent (e.g., sperm DNA, cot-1 DNA, etc.) during the hybridization to reduce non-specific binding. In a particularly preferred embodiment, the hybridization is performed in the presence of about 0.5 mg/ml DNA (e.g., herring sperm DNA). The use of blocking agents in hybridization is well known to those of skill in the art (see, e.g., Chapter 8 in P. Tijssen, supra.)

The stability of duplexes formed between RNAs or DNAs are generally in the order of RNA:RNA>RNA:DNA>DNA:DNA, in solution. Long probes have better duplex stability with a target, but poorer mismatch discrimination than shorter probes (mismatch discrimination refers to the measured hybridization signal ratio between a perfect match probe and a single base mismatch probe). Shorter probes (e.g, 8-mers) discriminate mismatches very well, but the overall duplex stability is low.

Altering the thermal stability ($T_m$) of the duplex formed between the target and the probe using, e.g., known oligonucleotide analogues allows for optimization of duplex stability and mismatch discrimination. One useful aspect of altering the $T_m$ arises from the fact that adenine-thymine (A-T) duplexes have a lower $T_m$ than guanine-cytosine (G-C) duplexes, due in part to the fact that the A-T duplexes have 2 hydrogen bonds per base-pair, while the G-C duplexes have 3 hydrogen bonds per base pair. In heterogeneous oligonucleotide arrays in which there is a non-uniform distribution of bases, it is not generally possible to optimize hybridization for each oligonucleotide probe simultaneously. Thus, in some embodiments, it is desirable to selectively destabilize G-C duplexes and/or to increase the stability of A-T duplexes. This can be accomplished, e.g., by substituting guanine residues in the probes of an array which form G-C duplexes with hypoxanthine, or by substituting adenine residues in probes which form A-T duplexes with 2,6 diaminopurine or by using the salt tetramethyl ammonium chloride (TMACl) in place of NaCl.

Altered duplex stability conferred by using oligonucleotide analogue probes can be ascertained by following, e.g., fluorescence signal intensity of oligonucleotide analogue arrays hybridized with a target oligonucleotide over time. The data allow optimization of specific hybridization conditions at, e.g., room temperature (for simplified diagnostic applications in the future).

Another way of verifying altered duplex stability is by following the signal intensity generated upon hybridization with time. Previous experiments using DNA targets and DNA chips have shown that signal intensity increases with time, and that the more stable duplexes generate higher signal intensities faster than less stable duplexes. The signals reach a plateau or "saturate" after a certain amount of time due to all of the binding sites becoming occupied. These data allow for optimization of hybridization, and determination of the best conditions at a specified temperature.

Methods of opting hybridization conditions are well known to those of skill in the art (see, e.g., *Laboratory Techniques in Biochemisby and Molecular Biology, Vol.* 24: *Hybridization With Nucleic Acid Probes*, P. Tijssen, ed. Elsevier, N.Y., (1993)).

(C) Signal Detection

In a preferred embodiment, the hybridized nucleic acids are detected by detecting one or more labels attached to the sample nucleic acids. The labels may be incorporated by any of a number of means well known to those of skill in the art. However, in a preferred embodiment, the label is simultaneously incorporated during the amplification step in the preparation of the sample nucleic acids. Thus, for example, polymerase chain reaction (PCR) with labeled primers or labeled nucleotides will provide a labeled amplification product. In a preferred embodiment, transcription amplification, as described above, using a labeled nucleotide (e.g. fluorescein-labeled UTP and/or CTP) incorporates a label into the transcribed nucleic acids.

Alternatively, a label may be added directly to the original nucleic acid sample (e.g., mRNA, polyA mRNA, cDNA, etc.) or to the amplification product after the amplification is completed. Means of attaching labels to nucleic acids are well known to those of skill in the art and include, for example nick translation or end-labeling (e.g. with a labeled RNA) by kinasing of the nucleic acid and subsequent attachment (ligation) of a nucleic acid linker joining the sample nucleic acid to a label (e.g., a fluorophore).

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like), radiolabels (e.g., $^3H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label. One particular preferred methods uses colloidal gold label that can be detected by measuring scattered light.

The label may be added to the target (sample) nucleic acid(s) prior to, or after the hybridization. So called "direct labels" are detectable labels that are directly attached to or incorporated into the target (sample) nucleic acid prior to hybridization. In contrast, so called "indirect labels" are joined to the hybrid duplex after hybridization Often, the indirect label is attached to a binding moiety that has been attached to the target nucleic acid prior to the hybridization. Thus, for example, the target nucleic acid may be biotinylated before the hybridization. After hybridization, an aviden-conjugated fluorophore will bind the biotin bearing hybrid duplexes providing a label that is easily detected. For a detailed review of methods of labeling nucleic acids and detecting labeled hybridized nucleic acids see *Laboratory Techniques in Biochemistry and Molecular Biology, Vol. 24: Hybridization With Nucleic Acid Probes*, P. Tijssen, ed. Elsevier, N.Y., (1993)).

Fluorescent labels are preferred and easily added during an in vitro transcription reaction. In a preferred embodiment, fluorescein labeled UTP and CTP are incorporated into the RNA produced in an in vitro transcription reaction as described above.

Means of detecting labeled target (sample) nucleic acids hybridized to the probes of the high density array are known to those of skill in the art. Thus, for example, where a colorimetric label is used, simple visualization of the label is sufficient. Where a radioactive labeled probe is used, detection of the radiation (e.g. with photographic film or a solid state detector) is sufficient.

In a preferred embodiment, however, the target nucleic acids are labeled with a fluorescent label and the localization of the label on the probe array is accomplished with fluorescent microscopy. The hybridized array is excited with a light source at the excitation wavelength of the particular fluorescent label and the resulting fluorescence at the emission wavelength is detected. In a particularly preferred embodiment, the excitation light source is a laser appropriate for the excitation of the fluorescent label.

The confocal microscope may be automated with a computer-controlled stage to automatically scan the entire high density array. Similarly, the microscope may be equipped with a phototrasducer (e.g. a photomultiplier, a solid state array, a CCD camera, etc.) attached to an automated data acquisition system to automatically record the fluorescence signal produced by hybridization to each oligonucleotide probe on the array. Such automated systems are described at length in U.S. Pat. No. 5,143,854, PCT Application 2092/10092, and copending U.S. application Ser. No. 08/195,889 filed on Feb. 10, 1994. Use of laser illumination in conjunction with automated confocal microscopy for signal detection permits detection at a resolution of better than about 100 $\mu$m, more preferably better than about 50 $\mu$m, and most preferably better than about 25 $\mu$m.

One of skill in the art will appreciate that methods for evaluating the hybridization results vary with the nature of the specific probe nucleic acids used as well as the controls provided. In the simplest embodiment, simple quantification of the fluorescence intensity for each probe is determined. This is accomplished simply by measuring probe signal strength at each location (representing a different probe) on the high density array (e.g., where the label is a fluorescent label, detection of the amount of florescence intensity) produced by a fixed excitation illumination at each location on the array). Comparison of the absolute intensities of an array hybridized to nucleic acids from a "test" sample with intensities produced by a "control" sample provides a measure of the relative expression of the nucleic acids that hybridize to each of the probes.

One of skill in the art, however, will appreciate that hybridization signals will vary in strength with efficiency of hybridization, the amount of label on the sample nucleic acid and the amount of the particular nucleic acid in the sample. Typically nucleic acids present at very low levels (e.g., <1pM) will show a very weak signal. At some low level of concentration, the signal becomes virtually indistinguishable from background. In evaluating the hybridization data, a threshold intensity value may be selected below which a signal is not counted as being essentially indistinguishable from background.

Where it is desirable to detect nucleic acids expressed at lower levels, a lower threshold is chosen. Conversely, where only high expression levels are to be evaluated a higher threshold level is selected. In a preferred embodiment, a suitable threshold is about 10% above that of the average background signal.

In addition, the provision of appropriate controls permits a more detailed analysis that controls for variations in hybridization conditions, cell health, non-specific binding and the like. Thus, for example, in a preferred embodiment, the hybridization array is provided with normalization controls. These normalization controls are probes complementary to control sequences added in a known concentration to the sample. Where the overall hybridization conditions are poor, the normalization controls will show a smaller signal reflecting reduced hybridization. Conversely, where hybridization conditions are good, the normalization controls will provide a higher signal reflecting the improved hybridization. Normalization of the signal derived from other probes in the array to the normalization controls thus provides a control for variations in hybridization conditions. Typically, normalization is accomplished by dividing the measured signal from the other probes in the array by the average signal produced by the normalization controls. Normalization may also include correction for variations due to sample preparation and amplification. Such normalization may be accomplished by dividing the measured signal by the average signal from the sample preparation/amplification control probes (e.g., the Bio B probes). The resulting values may be multiplied by a constant value to scale the results.

As indicated above, the high density array can include mismatch controls. In a preferred embodiment, there is a mismatch control having a central mismatch for every probe (except the normalization controls) in the array. It is expected that after washing in stringent conditions, where a perfect match would be expected to hybridize to the probe, but not to the mismatch, the signal from the mismatch controls should only reflect non-specific binding or the presence in the sample of a nucleic acid that hybridizes with the mismatch. Where both the probe in question and its corresponding mismatch control both show high signals, or the mismatch shows a higher signal than its corresponding test probe, there is a problem with the hybridization and the signal from those probes is ignored. The difference in hybridization signal intensity between the target specific probe and its corresponding mismatch control is a measure of the discrimination of the target-specific probe. Thus, in a preferred embodiment, the signal of the mismatch probe is subtracted from the signal from its corresponding test probe to provide a measure of the signal due to specific binding of the test probe.

The concentration of a particular sequence can then be determined by measuring the signal intensity of each of the probes that bind specifically to that gene and normalizing to the normalization controls. Where the signal from the probes is greater than the mismatch, the mismatch is subtracted. Where the mismatch intensity is equal to or greater than its corresponding test probe, the signal is ignored. The expression level of a particular gene can then be scored by the number of positive signals (either absolute or above a threshold value), the intensity of the positive signals (either absolute or above a selected threshold value), or a combination of both metrics (e.g., a weighted average).

In some preferred embodiments, a computer system is used to compare the hybridization intensities of the perfect match and mismatch probes of each pair. If the gene is expressed, the hybridization intensity (or affinity) of a perfect match probe of a pair should be recognizably higher than the corresponding mismatch probe. Generally, if the hybridizations intensities of a pair of probes are substantially the same, it may indicate the gene is not expressed. However, the determination is not based on a single pair of probes, the determination of whether a gene is expressed is based on an analysis of many pairs of probes.

After the system compares the hybridization intensity of the perfect match and mismatch probes, the system indicates expression of the gene. As an example, the system may indicate to a user that the gene is either present (expressed), marginal or absent (unexpressed). Specific procedures for data analysis is disclosed in U.S. application Ser. No. 08/772,376, previously incorporated for all purposes.

In addition to high density nucleic acid arrays, other methods are also useful for massive gene expression monitoring. Differential display, described by Liang, P. and Pardee, A. B. Differential Display of eukaryotic messenger RNA by means of the polymerase chain reaction. *Science* 257:967–971, 1992, incorporated herein by reference for all purposes) provides a useful mean for distinguishing gene expression between two samples. Serial analysis of gene expression, described by Velculescu et al. (Serial Analysis of Gene Expression. Science, 270:484–487, 1995, incorporated herein by reference for all purposes) provides another method for quantative and qualitative analysis of gene expression. Optical fiber oligonucleotide sensors, described by Ferguson et al. (A Fiber-optic DNA biosensor microarray for the analysis of gene expression. Nature-Biotechnology 14:1681–1684, 1996), can also be used for gene expression monitoring.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

EXAMPLES

Biomedical research has been aided tremendously by three developments: (i) the ability to generate small molecule libraries using combinatorial chemistry methods coupled with high-throughput screening, (ii) the enormous increase in the number of newly identified gene sequences from a host of different organisms, and (iii) the use of structural methods for the detailed characterization ofligand-protein interaction sites that can be exploited for ligand design. Here we applied these methods to the synthesis and characterization of potent, selective inhibitors of protein kinases involved in cell cycle control. The central role that cyclin-dependent kinases (CDKs) play in the timing of cell division and the high incidence of genetic alteration of CDKs or deregulation of CDK inhibitors in a number of cancers make CDKs a promising target for the design of selective inhibitors. Our approach to inhibiting CDKs has been to block the adenosine triphosphate (ATP)-binding site with compounds derived from combinatorial libraries of 2,6,9-trisubstituted purines. This strategy was motivated by the binding mode of the purine olomoucine, which exhibits good selectivity but only moderate inhibition [$IC_{50}$ (50% kinase inhibition)=7 $\mu$M] of a subset of the CDK family of protein kinases (1). The orientation of the purine ring of olomoucine within the ATP-binding site of CDK2 is rotated almost 160° relative to that of the adenosine ring of ATP. Thus, it seemed that the introduction of new substituents at the 2,6, and 9 positions of the purine ring, rather than substituents appended to the ribose, as is normally done, might lead to enhanced binding affinity and selectivity. A combinatorial approach to modifying the purine scaffold could be valuable in the search for potent and selective inhibitors of various cellular processes because of the ubiquitous occurrence of enzymes that use purines, including the estimated 2000 kinases encoded in the human genome.

To examine the effects of a range of diverse substituents on the purine ring, we synthesized combinatorial libraries in which the 2, 6, and 9 positions could be varied starting with a 2-fluoro-6-chloropurine framework (FIG. 1A)(2, 3). Substitution chemistry was used to install amines at the 2 and 6 positions, and a Mitsunobu reaction (4, 5) was used to alkylate the N9 position of the purine core. The substitution chemistry allows introduction of primary and secondary amines bearing a wide range of functional groups, whereas the Mitsunobu reaction tolerates primary and secondary alcohols lacking additional acidic hydrogens. Newly appended groups can be modified combinatorially in subsequent steps with a variety of chemistries including acylation, reductive amination, and Suzuki coupling reactions (6). During library synthesis, one position is held invariant to allow attachment to the solid support. Libraries are synthesized in a spatially separated format with either a pin apparatus (7) or polystyrene resin and screened for kinase inhibitors with a 96-well, solution-phase phosphorylation assay. FIG. 1. (A) Scheme for the combinatorial synthesis of 2,6,9-trisubstituted purines from a 2-, 6-, or 9-linked purine scaffold with amination and alkylation chemistries. Chemical structures of CDK inhibitors (B) flavopiridol (C) olomoucine and roscovitine, and (D) purvalanol A and B and (E) Compound 40 and (FIG. 1F) Compounds 100 and 101.

Several purine libraries in which the 2, 6, and 9 substituents were varied separately were iteratively synthesized and screened. We identified aA number of 3- and 4-substituted benzylamine and aniline substituents that lead to significant improvements in CDK2 binding when introduced at the 6 position of the purine ring. For example, replacement of the benzylamino group of olomoucine at the C6 position with 3-chloroaniline resulted in a 10-fold increase in the $IC_{50}$. Although a variety of hydroxyalkylamino, dihydroxyalkylamino, and cycloalkylamino substituents at the 2 position resulted in moderate improvements in binding affinity, greater increases were achieved with amino alcohols derived from alanine, valine, and isoleucine. For example the R-isopropyl side chain of valinol resulted in a 6.5-fold increase relative to the hydroxyethyl substituent of olomoucine. In contrast to many protein kinases that can accommodate larger substituents at the N9 of the purine ring, CDK2 binding was strongest for those purines bearing small alkyl or hydroxyalkyl substituents. Those substituents that resulted in the most potent CDK2 inhibition were combined in second-generation libraries by solution-phase chemistry. The $IC_{50}$ data for these series of compounds indicate that the inhibitory effects of these substituents are approximately additive.

Currently, our most potent inhibitor, 2-(1R-isopropyl-2-hydroxyethylamino)-6-(3-chloro4-carboxyanilino)-9-isoprop ylpurine (purvalanol B, FIG. 1D), has an $IC_{50}$ against the complex of CDK2-cyclin A of 6 nM, which corresponds to a 1000-fold increase over olomoucine and a 30-fold increase over flavopiridol (FIG. 1B), one of the most potent and selective CDK2 inhibitors known and currently in human clinical trials (8). Purvalanol B shows a high degree of selectivity: among the 22 human purified kinases tested (1, 9), only a subset of the CDKs (cdc2-cyclin B, CDK2-cyclin A, CDK2-cyclin E, CDK5-p35) were significantly inhibited (Table 1). Several close analogs of purvalanol B were also potent inhibitors of cdc2 and CDK2, including the more membrane permeable analog purvalanol A and compound 52 [(2-(2-hydroxyethylamino)-6(3-chloroanilino)-9-isopropylpurine, $IC_{50}$=340 nM against cdc2-cyclin B] (Table 2). We also assessed the selectivity of purvalanol A, compound 52, and a N6-methylated version of compound 52 (52Me) against four yeast CDKs (10) (Cdc28p, Kin28p, Pho85p, and Srb10p) and the related kinase Cak1p using kinase assays performed in immunoprecipitates (Table2) (11). Of the yeast kinases tested, only the cell cycle-regulating kinase Cdc28p and the highly homologousPho85p kinase (50% identity to Cdc28p), which is involved in phosphate metabolism, were inhibited by purvalanol A and 52. Compound 52Me did not inhibit any of the CDKs tested.

TABLE 1

$IC_{50}$ values for purvalanol (purv.) A and B
for a variety of purified kinases.

| Kinase | Purv. A ($IC_{50}$ nM) | Purv. B ($IC_{50}$ nM) |
|---|---|---|
| cdc2-cyclin B | 4 | 6 |
| cdc2-cyclin B (150 μM ATP) | 40 | 50 |
| cdc2-cyclin B (1.5 mM ATP) | 500 | 250 |
| cdk2-cyclin A | 70 | 6 |
| cdk2-cyclin E | 35 | 9 |
| cdk4-cyclin D1 | 850 | >10,000 |
| cdk5-p35 | 75 | 6 |
| erk1 | 9,000 | 3,333 |
| c-jun $NH_2$-terminal kinase | >1,000 | >10,000 |
| Protein kinase C | >10,000 | >100,000 |
| Protein kinase C1 | >10,000 | >100,000 |
| Protein kinase C2 | >10,000 | >100,000 |
| Protein kinase C | >10,000 | >100,000 |
| Protein kinase C | >100,000 | >100,000 |
| Protein kinase C | >100,000 | >100,000 |
| Protein kinase C | >100,000 | >100,000 |
| Protein kinase C | >100,000 | >100,000 |
| cAMP-dependent protein kinase | 9,000 | 3,800 |
| cGMP-dependent protein kinase | >10,000 | >100,000 |

TABLE 1-continued $IC_{50}$ values for purvalanol (purv.) A and B
for a variety of purified kinases.

| Kinase | Purv. A ($IC_{50}$ nM) | Purv. B ($IC_{50}$ nM) |
|---|---|---|
| Casein kinase 1 | >3,333 | >3,333 |
| GSK3- | >10,000 | >10,000 |
| Insulin-receptor tyrosine kinase | 5,000 | 2,200 |

TABLE 2

$IC_{50}$ values for 52 and 52Me for immunoprecipitated yeast kinases.

| Kinases | 52 ($IC_{50}$ μM) | 52Me ($IC_{50}$ μM) |
|---|---|---|
| Cdc28p | 7 | >500 |
| Pho85p | 2 | >500 |
| Kin28p | >500 | >500 |
| Srb10 | >500 | >500 |
| Cak1p | >500 | >500 |

Figure 1A:
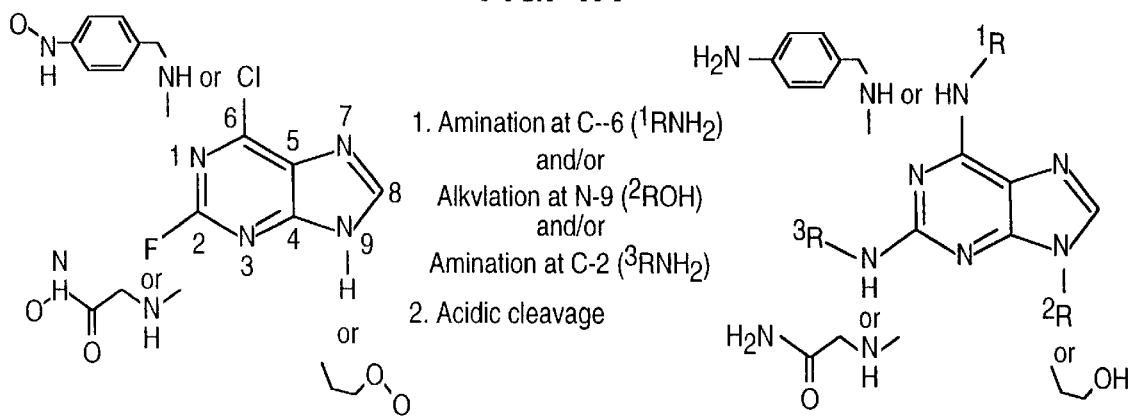
(FIG. 1A) Scheme for the combinatorial synthesis of 2,6,9-trisubstituted purines from a 2-, 6-, or 9-linked purine scaffold with amination and alkylation chemistries. Chemical structures of CDK inhibitors (FIG. 1B) flavopiridol (FIG. 1C) olomoucine and roscovitine, and (FIG. 1D) purvalanol A and B and (FIG. 1E) Compound 40 and (FIG. 1F) Compounds 100 and 101.
Figure 1B:
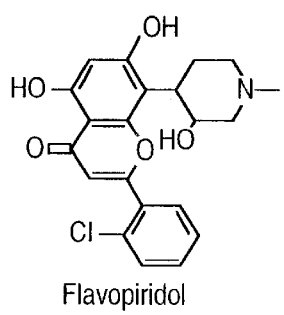
FIG. 1.
Figure 1C:
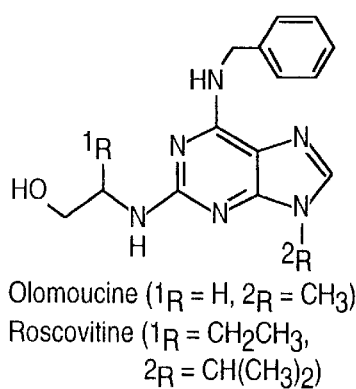
Figure 1D:
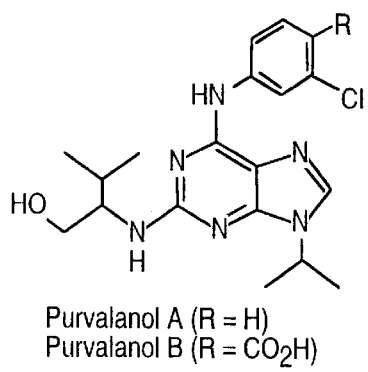
Figure 1E:
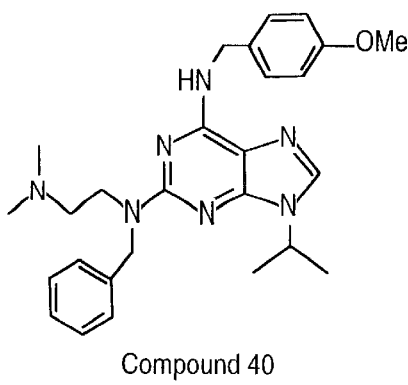
Figure 1F:
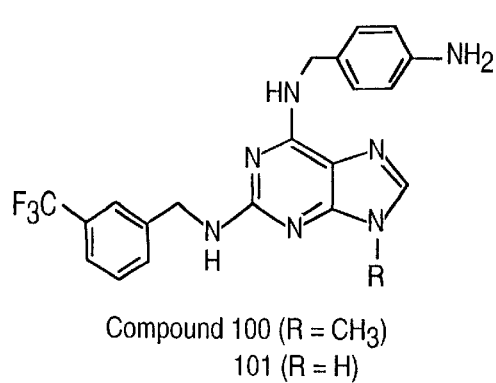
Figure 2A:
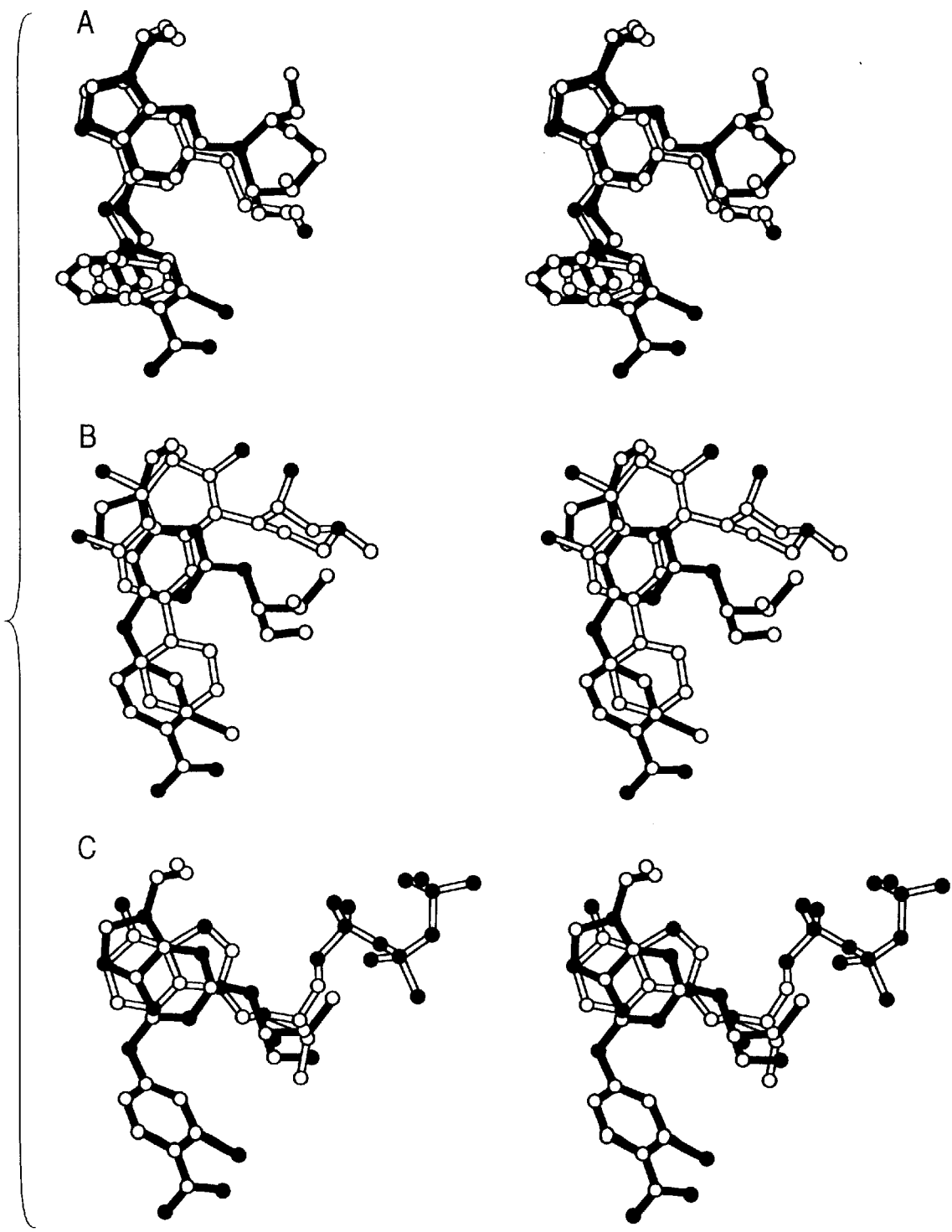
(FIG. 2A) Purvalanol B bound to CDK2 (black sticks, principal conformation only) is compared with bound (1) olomoucine (white sticks) and bound roscovitine (orange sticks), (2) bound flavopiridol (green sticks), and (3) bound ATP (yellow sticks). The comparisons are based on superposition of the C atoms of CDK2. The ligands are shown in ball-and-stick representation with carbon atoms colored white, nitrogen atoms colored blue, oxygen atoms colored red, phosphorous atoms colored violet, and the chlorine atom of purvalanol colored green.
Figure 2B:
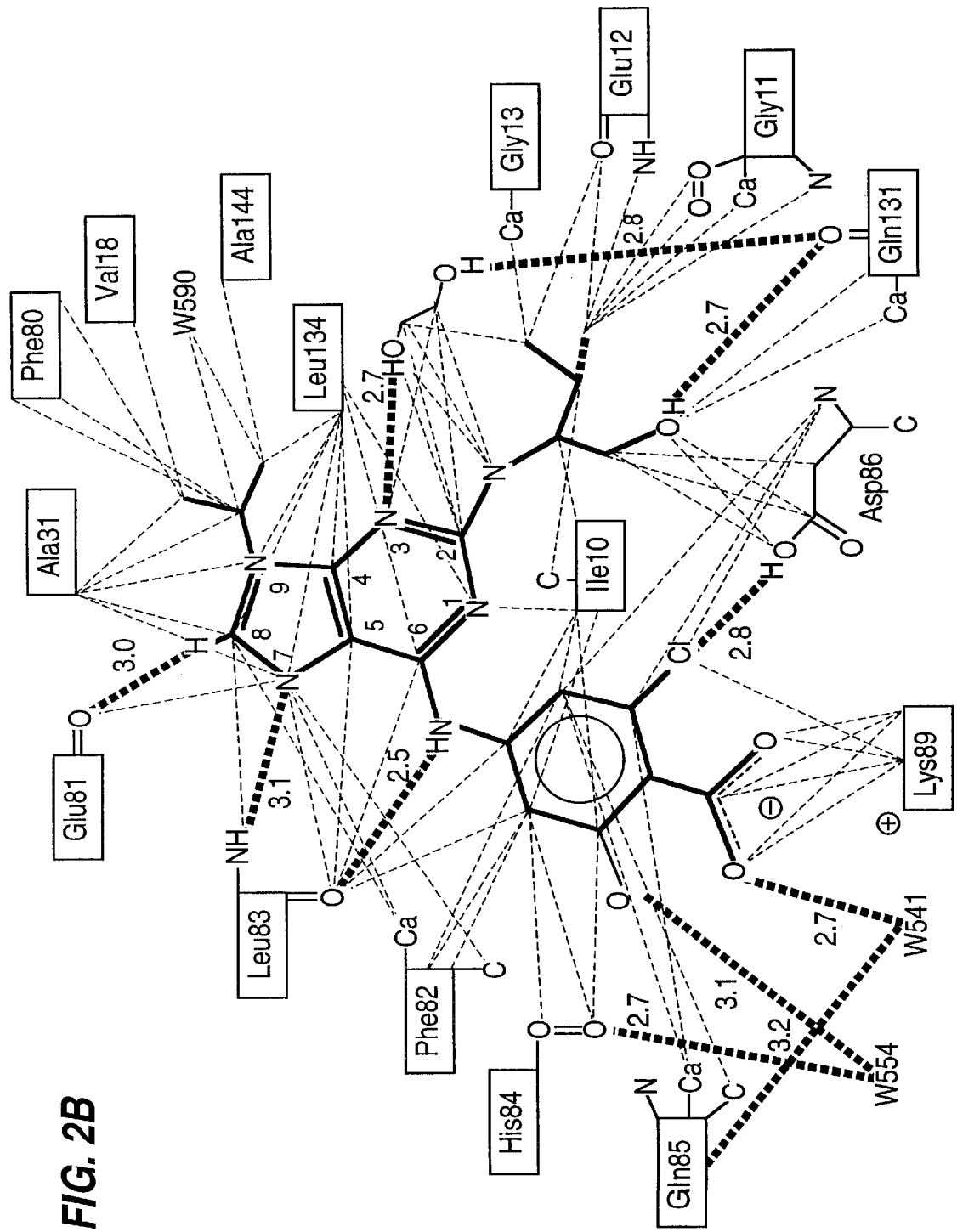
(FIG. 2B) Schematic drawing of CDK2-purvalanol B interactions. Protein side chain contacts are indicated by lines connecting the respective residue box and interactions to main chain atoms are shown as lines to the specific main chain atoms. Van der Waals contacts are indicated by thin dotted lines, and H bonds by dashed lines. For H bonds the distances between the nonhydrogen atom are indicated in angstroms. W, water.

To explore the structural basis for the selectivity and affinity of these inhibitors we determined the crystal structure of the human CDK2-purvalanol B complex to 2.05 Å resolution (12) (FIG. 2). The electron density map shows that binding of purvalanol B to the CDK2 crystals is well ordered except for the 3-chloroanilino group, which appears to be bound in two alternative conformations (FIG. 2). Purvalanol B fits snugly into the ATP-binding site, as is evident by the 86% complementarity between the surface area buried by the inhibitor (364 $Å^2$) compared with the available binding surface in the active site of the protein (423 $Å^2$). The overall geometry of purvalanol B bound to CDK2 resembles that of the related adenine-substituted inhibitors in the CDK2-olomoucine and CDK2-roscovitine complexes, with the purine ring and its C2, N6, and N9 substituents occupying similar binding pockets. The purine ring makes mostly hydrophobic and van der Waals contacts with CDK2 residues. A pair of conserved H bonds are present between the N7 imidazole nitrogen and the backbone NH of $Leu^{83}$, and between the N6 amino group and the backbone carbonyl of $Leu^{83}$; this latter interaction likely accounts for the greatly reduced inhibitory activity resulting from methylation of N6 in compound 52Me. Furthermore, all three 2,6,9-trisubstituted adenines form a H bond between the acidic C8 atom of the purine ring and the carbonyl oxygen of $Glu^{81}$, an infrequently observed interaction in the crystal structures of nucleic acids and proteins (13).

The C2 side chain of purvalanol B is bound in the ATP ribose-binding pocket (FIG. 2A, structure 3), with the R-isopropyl group closely packed against backbone atoms of the glycine-rich loop and the hydroxyl group making a H bond with the backbone carbonyl of $Gln^{131}$. The R-isopropyl side chain of purvalanol B leads to a significant repositioning of the C2 substituent relative to the R-ethyl substituent of roscovitine (FIG. 2A, structure 1), resulting in an open pocket in the active site lined by the polar side chains of $Lys^{33}$, $Asn^{132}$, and $Asp^{145}$. In the CDK2-flavopiridol complex, this region is occupied by the N-methylpiperidinyl ring of the inhibitor (FIG. 2A, structure 2), suggesting that further increases in affinity of purvalanol B may result from appending substituents at the C2 position that interact with this site. The 3-chloroanilino group at N6 of purvalanolB points toward the outside of the ATP-binding pocket, a region not occupied in the CDK2-ATP complex. Interactions in this region are likely responsible for the increased affinity and selectivity of the inhibitors compared with ATP and are evident in the CDK2 complexes of flavopiridol, olomoucine, and roscovitine as well. In the CDK2-purvalanol B complex, the 3-chloroanilino group of the inhibitor is packed tightly against the side chains of Ile[10] and Phe[82]. Further stabilization of the binding of the 3-chloroanilino group comes from a polar interaction between the Cl and the side chain of Asp[86], which appears to be present in about two-thirds of the molecules in the CDK2-purvalanol B crystals. In the other conformation the phenyl ring of the 3-chloroanilino group is flipped ~160°, suggesting a partially protonated state of Asp[86]. In addition to improved packing interactions, the increased binding affinity of purvalanol B relative to olomoucine may result from steric constraints imposed by the purine and chlorinated aniline ring systems that limit the number of conformations of the inhibitor. Numerous substituents at the 4 position of the aniline ring were tolerated, consistent with the solvent accessibility of this site, which makes this position an obvious candidate for altering both the solubility and membrane permeability. Finally, the N9 isopropyl group of purvalanol B packs in a small hydrophobic pocket formed by the side chains of Val[18], Ala[31], Phe[80], Leu[134], and Ala[144], consistent with the narrow range of substituents that can be tolerated at this position.

To determine the cellular effects of these CDK-directed cell cycle inhibitors, we tested purvalanol A on the NCI panel of 60 human tumor cell lines (leukemia, non-small cell lung cancer, colon cancer, renal cancer, prostate cancer, and breast cancer). Although the average $GI_{50}$(50% growth inhibition) is 2 $\mu$M, two cell lines out of the 60 showed an ~20-fold increase in sensitivity to purvalanol A: the KM12 colon cancer cell line with a $GI_{50}$ of 76 nM and the NCI-H522 non-small cell lung cancer cell line with a $GI_{50}$ of 347 nM.

Fluorescence-activated cell sorting (FACS) analysis of human lung fibroblast cells treated with a structural analog of purvalanol A, 2-(bis-(hydroxylethyl) amino)-6-(4-methoxybenzylamino)-9-isopropylpurine, exhibited both $G_1$-S and $G_2$-M inhibitory activity at high concentrations and predominant $G_1$-S inhibition at lower concentrations (14). Significant inhibition was also observed in *Saccharomyces cerevisiae*, where compound 52 inhibited growth in a drug-sensitized yeast strain (15) with a $GI_{50}$ of 30 $\mu$M. In contrast, the closely related compound 52Me proved to be a significantly weaker inhibitor of yeast growth ($GI_{50}$=200 $\mu$M) (16).

Conclusion

It is to be understood that the above description is intended to be illustrative and not restrictive. Many variations of the invention will be apparent to those of skill in the art upon reviewing the above description. By way of example, the invention has been described primarily with reference to the use of a high density oligonucleotide array, but it will be readily recognized by those of skill in the art that other nucleic acid arrays, other methods of measuring transcript levels and gene expression monitoring at the protein level could be used. The scope of the invention should, therefore, be determined not with reference to the above description, but should instead be determined with reference to the appended claims, along with the fill scope of equivalents to which such claims are entitled.

REFERENCES AND NOTES

1. J. Vesely, etal., *Eur. J Biochem.* 224, 771(1994); L. Meijer, et al., ibid 243, 527 (1997).
2. N. S. Gray, S. Kwon, P. G. Schultz, *Tetrahedon Lett.* 38, 1161 (1997)
3. T. C. Norman, N. S. Gray, J. T. Koh, *J Am. Chem. Soc.* 118, 7430 (1996).
4. O. Mitsonobu, *Synthesis* 1, 1 (1981).
5. A. Toyota, N. Katagiri, C. Kaneko, *Heterocycles* 36, 1625 (1993).
6. B. J. Backes and J. A. Ellman, *J. Am. Chem. Soc.* 116, 11171 (1994)
7. H. M. Geysen, S. J. Rodda, T. J. Mason, G. Tribbick, P. G. J. Schoofs, *Immunol. Methods* 102, 259 (1987).
8. L. Meijer, *Trends in Cell Biol.* 6, 393 (1996).
9. Starfish is the major source for cdc2 cyclin B kinase. The recombinant human cdc2-cyclin B is likely to contain inactive monomers and dimers that would interfere with CDK inhibition assays [see (11)].
10. D. O. Morgan, *Annu. Rev. Cell Dev. Biol.* 13, 261 (1997).
11. Supplemental material is available at http://www.sciencemag.org/featureldata/976815.shl.
12. Crystallography statistics for the CDK-purvalanol B complex. Data: space group, P212121, cell constants a=53.55 Å, b=71.35 Å, c=72.00 Å, resolution 32 to 2.05 Å. Number of unique reflections=17655, completeness=98.7% (91.6 from 2.11 to 2.05 Å), $R_{merge}=_{hi}I_{hi} I_h|_{hi}I_{hi}$=5.5%, where h are unique reflections indices and i indicate symmetry equivalent indices. Refinement calculations: $R_{factor}=(F_oF_c)F_o$=18.8%, where $F_o$ and $F_c$ are the observed and calculated structure factors, respectively; $R_{free}$=26.4% (same calculation as for $R_{factor}$, but with 5% of the data); average atomic B values for protein: 31.4 Å$^2$, inhibitor=32.2 Å$^2$, waters=37.7 Å$^2$. Observed deviations: root means square (rms) bond lengths=0.008 Å; rms bond angles= 1.31°. The final model includes 279 residues of CDK2 (residues 36 to 43 and 153 to 163 are not included because of weak or missing electron density), purvalanol B, 91 water molecules, and one molecule of ethyleneglycol. Efforts to crystallize the CDK2-purvalanol A complex resulted crystals of poor quality.
13. M. C. Wahl and M. Sundaralingam, *Trends Biochem. Sci.* 22, 97 (1997).
14. E. E. Brooks, etal., *J Biol. Chem.* 272, 29207 (1997).
15. Because of weak inhibition of yeast growth by flavopiridol we used a strain with three drug-sensitizing deletions (erg6,pdr5, snq2). This strain showed $GI_{50}$ for 52 and flavopiridol at concentrations of 30 and 7 $\mu$M, respectively. Three cultures [110 ml, in yeast extract, peptone, and dextrose (YPD)] were inoculated with single colonies of YRP1 (MAT, erg6::LEU2, pdr5::TRP1, snq2::HIS6) and grown at 30° C. with constant agitation in a water bath incubator. When the cell density reached an optical density (OD) of 0.9 (at a wavelength of 600 nm), 27.5 $\mu$l of a 100 mM dimethyl sulfoxide (DMSO) stock solution of 52 or flavopiridol or DMSO alone was added. After 2 hours the cells were harvested by centrifugation and flash frozen with liquid nitrogen. For the temperature-sensitive cdc28 mutants, three cultures (75 ml, YPD) of AFS 199 (cdc28-13), AA104 (cdc28-4), and their isogenic background strain AFS34 (MATa, ade2-1, his3-11, leu2-3, trp1-1, ura3) were grown from single colonies to an OD of 0.9 (600 nm) and harvested as described. Frozen cells were stored at 80° C.
16. The diminished growth inhibitory activity of compound 52Me is unlikely to result from poorer bioavailability because a similar N6 methylation is observed to increase the in vivo potency of a related series of purine-based inhibitors. The residual growth inhibitory activity of 52Me likely reflects activity against other cellular targets. Compounds 52, 52Me, and flavopiridol failed to cause a uniform arrest morphology in yeast. FACS analysis also did not reveal synchronization of yeast cells after treatment with 52 or 52Me, which may be due to inhibition of a variety CDKs responsible for different cell cycle transitions (as is observed in FACS experiments on mammalian cells) or activity against other targets not specifically examined in vitro.

17. D. J. Lockhart et al., Nature Biotechnol. 14, 1675 (1996).
18. L. Wodicka, H. Dong, M. Mittmann, M.-H. Ho, D. J. Lockhart, ibid 15, 1359 (1997).
19. J. L. DeRisi, V. R. Iyer, P. O. Brown, Science 278, 680 (1997).
20. S. P. A. Fodor, et al., ibid 251, 767 (1991
21. Transcripts that showed a significant and reproducible change in concentration (greater than twofold) in cells treated with the compounds between triplicate hybridizations for each of at least two independent experiments were examined further.
22. F. R. Cross, Curr. Opion. Cell Biol. 7, 790 (1995).
23. A. J. Van Wijnen, et al., Proc. Natl. Acad Sci. U.S.A. 91, 12882 (1994).
24. E. M. Lenburg and E. K. O'Shea, Trends Biol. Sci. V21 383 (1996).
25. L. W. Bergman and B. K. Timblin, Mol. Microbiol. 26, 981 (1997).
26. L. W. Bergman, K. Tatchell, B. K. Timblin, Genefics 143, 57 (1996).
27. Because the PHO85 gene is nonessential it should be possible to determine if these inductions are a direct consequence of Pho85p kinase inhibition by determining if the same inductions are seen after treating with inhibitor in a strain lacking the kinase.
28. B. Andrews, et al., Mol. Cell Biol. 17, 1212 (1997).
29. P. Mazur, et al., ibid 15, 5671 (1995).
30. Transcript profiles were also measured for the cdc28 temperature-sensitive allele cdc28-13. The cdc28-13 strain contains an arginine to asparagine mutation at residue 283 near the COOH-terminus, which does not significantly affect kinase activity at the permissive temperature but does cause cell cycle arrest when switched to the nonpermissive temperature (32). The cdc28-13 strain showed very few changes in mRNA transcripts when compared with wild type at the permissive temperature. The levels of only 11 mRNAs changed by more than twofold, consistent withthe observation that this mutant has essentially wild-type kinase activity at 25° C. In addition, the nearly identical gene expression patterns obtained for the cdc28-13 and isogenic wild-type CDC28 strain demonstrate the reproducibility of these experiments.
31. The cdc284 allele that exhibits a START ($G_1$-S) defect or an allele such as cdc28-1N, which has a $G_2$-M defect could also serve as a mimic of CDK inhibition by 52 or flavopiridol.
32. S. I. Reed, J. A. Hadwiger, A. T. Lorincz, Proc. Natl. Acad Sci. U.S.A. 82, 4055 (1985).
33. C. Koch and K. Nasmyth, Curr. Opion. Cell Biol. 6, 451 (1994).
34. M. Russell, J. Bradshaw-Rouse, D. Markwardt, W. Heideman, Mol. Biol. Cell 4, 757 (1993).
35. H. Ruis and C. Schuller, BioEssays 17, 959 (1995).
36. J. R Woodgett, et al., Trends Biochem. Sci. 16, 177 (1991).
37. U.S. patent application Ser. No. 1,368,002
38. For example, using a screen of our purine libraries, to be described elsewhere, we have identified a compound that causes extensive depolymerization of microtubules and condensation of DNk
39. J. Rine, W. Hansen, E. Hardeman, R.W. Davis, Proc. Natl. Acad Sci. U.S.A. 80, 6750 (1983); M. Schena, D. Shalon, R.W. Davis, P. O. Brown, Science 270, 467 (1995).

TABLE 3

Effects of C52 + FLA + MUT 4

| | | |
|---|---|---|
| 1. | YBR214W | (Similar to S. pombe protein involved in meiosis + mitosis) |
| | INCREASES | (4–4.5 x for C52 |
| | | 7–8.5 x for FLA |
| | | 2–2.5 x MUT 4) |
| 2. | YBL002W | HTB2 Histope |
| | DECREASES | (~ 4.5 x for C52 |
| | | ~ 2.7 x for FLA |
| | | ~ 1.9 x for MUT 4) |
| 3. | YALO61W | alcohol/sorbitol dehydrogenase |
| | INCREASES | 9–11 x with C52 & FLA |
| | | ~ 6.1 x MUT 4 (not. detected in wt) |
| 4. | YKRO97W | PCK1 Phosphoenol pyruvate carboxykinase |
| | INCREASES: | ~ 7–8 fold with C52 |
| | | ~ 4 x with FLA |
| | | ~ 3.5 x MUT 4 |

C52 UNIQUE
1  YKLO71 W   unknown fund.
   7–12 x Increase (C52)
FLA UNIQUE
1.  YCRX13 W   SOL2
    7.5–10 x INCREASE
    *    ALSO MUT 4 2.3–2.7 x INC
    C52 - much smaller inc. (NL. 8 x at most)
MUT 4 specific
YOR202W   H153 2–4 X INC
CHANGES COMMON TO C52 AND FLA (Not mutants)
1.  YGR108 W (CLB1) = G2/M phase specific cyclin
    DECREASES        (~ 8 fold with C52
    ~ 2.5–3 fold with FLA)
2.  YNL327 W (EGT2) involved in cell separation
    DECREASES 2–3 fold (both drugs)
3.  YBR114W (RAD16) Nucleotide G2 repair
    INCREASES 4–5 X both drugs
4.  YDR247W Serine/Threonine Kinase similar to S. pombe RAN 1
    3–3.5 x INCREASE both drugs
5.  HXT5 Homologous to hexose transporters
    INCREASES
    Not detected in untreated (~ 12–14 x increase with drugs)
6.  YGRO43
    similar to Talp a transddolase

| | | |
|---|---|---|
| | | INCREASES ~ 4–7.5 x with drugs |
| 7. | YGL179 | INCREASES C52 & FLA |
| 8. | YBR296C | VERY LARGE INCREASE (15–25 x) |
| 9. | YLR178c (TFS1) | INCREASES ~ 6x |
| 10. | YDR281 C   C52 | ~4.5–5.5 x INCREASE |
| | MUT 4: | 3.5–5.5 x DECREASE |

We claim:

1. A method of comparing the effects of a drug to the effects of a mutation, comprising:

contacting a drug with a first population of cells;

preparing a transcription indicator from the first population of cells, wherein a transcription indicator is selected from the group consisting of cellular RNA, cellular mRNA, cRNA and cDNA;

preparing a transcription indicator from a second population of cells which population is not contacted with a drug, wherein the second population of cells carry a mutation in a gene of interest relative to the first population of cells;

preparing a transcription indicator from a third population of cells which is not contacted with a drug and which does not carry the mutation;

hybridizing the transcription indicators to oligonucleotide arrays to form a pattern of hybridization for each of said populations of cells;

comparing each of the first and the second populations' patterns of hybridization to the third population's pattern of hybridization to identify changes caused by the drug and the mutation;

comparing the changes caused by the drug to those caused by the mutation;

identifying the gene of interest as a candidate target of the drug if the drug and the mutation affect hybridization to one or more common oligonucleotides; identifying the drug as affecting targets other than the gene if the drug affects hybridization to both common oligonucleotides and unique oligonucleotides.

2. The method of claim 1 wherein the drug is flavopiridol.

3. The method of claim 1 wherein the drug is compound 52.

4. The method of claim 1 wherein the mutation is in a kinase.

5. The method of claim 1 wherein the mutation is in the CDC28 gene.

6. The method of claim 1 wherein the cells are yeast cells.

7. The method of claim 1 wherein the cells are mammalian cells.

8. The method of claim 1 wherein the array comprises at least 1000 oligonucleotides of distinct sequence.

9. The method of claim 1 wherein the array comprises at least 6000 oligonucleotides of distinct sequence.

10. A method of comparing the effects of a drug to the effects of a mutation, comprising:

comparing changes in expression caused by a drug to those caused by a mutation, wherein the changes in expression are determined by the process of:

contacting the drug with a first population of cells;

preparing a transcription indicator from the first population of cells, wherein a transcription indicator is selected from the group consisting of cellular RNA, cellular mRNA, cRNA and cDNA;

preparing a transcription indicator from a second population of cells which population is not contacted with a drug, wherein the second population of cells carry the mutation in a gene of interest relative to the first population of cells;

preparing a transcription indicator from a third population of cells which is not contacted with a drug and which does not carry the mutation;

hybridizing the transcription indicators to oligonucleotide arrays to form a pattern of hybridization for each of said populations of cells;

comparing each of the first and the second populations' patterns of hybridization to the third population's pattern of hybridization to identify changes caused by the drug and the mutation;

identifying the gene of interest as a candidate target of the drug if the drug and the mutation affect hybridization to one or more common oligonucleotides;

identifying the drug as affecting targets other than the gene if the drug affects hybridization to both common oligonucleotides and unique oligonucleotides.

11. The method of claim 10 wherein the drug is flavopiridol.

12. The method of claim 10 wherein the drug is compound 52.

13. The method of claim 10 wherein the mutation is in a kinase.

14. The method of claim 10 wherein the mutation is in the CDC28 gene.

* * * * *